(12) United States Patent
Lubbert et al.

(10) Patent No.: US 7,511,064 B2
(45) Date of Patent: *Mar. 31, 2009

(54) DERIVATIVES OF 4-(THIO- OR SELENOXANTHENE-9-YLIDENE)-PIPERIDINE OR ACRIDINE AND ITS USE AS A SELECTIVE 5-HT$_{2B}$ RECEPTOR ANTAGONIST

(75) Inventors: Hermann Lubbert, Leverkusen (DE); Christoph Ullmer, Bergisch Gladbach (DE); Emile Bellott, Beverly, MA (US); Mark Froimowitz, Newton Centre, MA (US); Douglas Gordon, Burlington, MA (US)

(73) Assignee: Biofrontera Bioscience GmbH, Leverkusen (DE)

( * ) Notice: Subject to any disclaimer, the term of this patent is extended or adjusted under 35 U.S.C. 154(b) by 335 days.

This patent is subject to a terminal disclaimer.

(21) Appl. No.: 11/379,353

(22) Filed: Apr. 19, 2006

(65) Prior Publication Data

US 2006/0183905 A1    Aug. 17, 2006

Related U.S. Application Data

(63) Continuation of application No. 10/281,415, filed on Oct. 25, 2002, now Pat. No. 7,060,711.

(60) Provisional application No. 60/343,817, filed on Oct. 25, 2001.

(51) Int. Cl.
*A61K 31/4535* (2006.01)
*C07D 409/04* (2006.01)

(52) U.S. Cl. ............... 514/324; 546/202; 546/104; 546/102; 546/62; 435/7.2; 514/297; 514/285; 514/183

(58) Field of Classification Search ............... 514/324, 514/297, 285, 183; 546/202, 104, 102, 62; 435/7.2
See application file for complete search history.

(56) References Cited

U.S. PATENT DOCUMENTS

| | | | |
|---|---|---|---|
| 3,275,640 A | 9/1966 | Engelhardt et al. | |
| 3,408,355 A | 10/1968 | Renz et al. | |
| 3,557,287 A | 1/1971 | Berde et al. | |
| 4,285,956 A | 8/1981 | Lassen et al. | |
| 4,777,177 A | 10/1988 | Traber et al. | |
| 7,060,711 B2 * | 6/2006 | Lubbert et al. | ............... 514/297 |

FOREIGN PATENT DOCUMENTS

| | | |
|---|---|---|
| DE | 22 56 392 | 5/1973 |
| EP | 0 005 607 | 11/1979 |
| FR | 2 290 202 | 8/1976 |
| GB | 1 000 509 | 8/1965 |
| IE | 42137 | 8/1980 |

* cited by examiner

*Primary Examiner*—Charanjit S Aulakh
(74) *Attorney, Agent, or Firm*—Knobbe Martens Olson & Bear LLP

(57) ABSTRACT

The present invention relates to derivatives of 4-(Thio- or Selenoxanthene-9-ylidene)-piperidine or acridine and pharmaceutically acceptable salts thereof, use of these compounds as a medicament and for the manufacture of a medicament for treatment of a disease state which can be alleviated by treatment with a 5-HT2B antagonist.

21 Claims, No Drawings

DERIVATIVES OF 4-(THIO- OR SELENOXANTHENE-9-YLIDENE)-PIPERIDINE OR ACRIDINE AND ITS USE AS A SELECTIVE 5-HT$_{2B}$ RECEPTOR ANTAGONIST

This application is a continuation of application Ser. No. 10/281,415, filed Oct. 25, 2002, which claims priority to Provisional Appl. No. 60/343,817, filed Oct. 25, 2001.

FIELD OF THE INVENTION

The present invention relates to derivatives of 4-(Thio- or Selenoxanthene-9-ylidene)-piperidine and acridine and pharmaceutically acceptable salts thereof, which exhibit useful pharmacological properties, including utility as selective 5-HT$_2$B receptor antagonists for treatment of a disease state which can be alleviated by treatment with a 5-HT$_{2B}$ receptor antagonist.

DESCRIPTION OF THE RELATED ART

Serotonin, a neurotransmitter with mixed and complex pharmacological characteristics, was first discovered in 1948, and subsequently has been the subject of substantial research. Serotonin, also referred to as 5-hydroxytryptamine (5-HT), acts both centrally and peripherally on discrete 5-HT receptors. Currently, fourteen subtypes of serotonin receptor are recognized and delineated into seven families, 5-HT$_1$, to 5-HT$_7$. Within the 5-HT$_2$ family, 5-HT$_{2A}$, 5-HT$_{2B}$ and 5-HT$_{2C}$ subtypes are known to exist. These subtypes share sequence homology and display similarities in their specificity for a wide range of ligands. Nomenclature and classification of 5-HT receptors have been reviewed in Martin & Humphrey 1994 *Neuropharm* 33:261-273; and Hoyer et al. 1994 *Pharm Rev* 46:157-203).

The 5-HT2B receptor, initially termed 5-HT$_{2F}$, or serotonin receptor like (SRL), was first characterized in rat isolated stomach fundus (Clineschmidt et al. 1985 *J Pharmacol Exp Ther* 235:696-708; Cohen & Wittenauer 1987 *J Cardiovasc Pharmacol* 10:176-181) and initially cloned from rat (Foguet et al. 1992 *EMBO* 11:3481-3487) followed by the cloning of the human 5-HT$_{2B}$ receptor (Schmuck et al. 1994 *FEBS Lett* 342:85-90; Kursar et al. 1994 *Mol Pharmacol* 46:227-234). The closely related 5-HT$_{2C}$ receptor, widely distributed in the human-brain, was first characterized as a 5-HT$_{1C}$ subtype (Pazos et al. 1984 *Eur J Pharmacol* 106:539-546) and was subsequently recognized as belonging to the 5-HT$_2$ receptor family (Pritchett et al. 1988 *EMBO J* 7:4135-4.140).

Because of the similarities in the pharmacology of ligand interactions at 5-HT$_{2B}$ and 5-HT$_{2C}$ receptors, many of the therapeutic targets that have been proposed for 5-HT$_{2C}$ receptor antagonists are also targets for 5-HT$_{2B}$ receptor antagonists. Current evidence strongly supports a therapeutic role for 5-HT$_{2B/2C}$ receptor antagonists in treating anxiety (e.g., generalized anxiety disorder, panic disorder and obsessive compulsive disorder), alcoholism and addiction to other drugs of abuse, depression, migraine, sleep disorders, feeding disorders (e.g., anorexia nervosa) and priapism. Additionally, current evidence strongly supports a therapeutic role for selective 5-HT$_{2B}$ receptor antagonists that will offer distinct therapeutic advantages collectively in efficacy, rapidity of onset and absence of side effects. Such agents are expected to be useful in the treatment of hypertension, disorders of the gastrointestinal track (e.g., irritable bowel syndrome, hypertonic lower esophageal sphincter, motility disorders), restenosis, asthma and obstructive airway disease, and prostatic hyperplasia (e.g., benign prostatic hyperplasia).

U.S. Pat. No. 3,275,640 describes generically substituted 1-hydrocarbyl-4-(9H-thioxanthene-9-ylidene)-piperidines and their preparation. It is also disclosed that the compounds may be used as therapeutic agents because of their antihistaminic and/or antiserotonin properties.

U.S. Pat. No. 3,557,287 relates to a combination preparation for use in the treatment of headaches of vascular origin containing as active constituents (a) a vasotonic lysergic acid selected from ergostine, ergotamine, dihydroergostine, dihydroergotamine, ergovaline, 5'-methylergoalanine; (b) caffeine; and (c) 9-(1-methyl-4-perperidylidene)thioxanthene (=1-methyl-4-(9H-thioxanthene-9-ylidene)-piperidine.

German patent DE 22 56 392 discloses 4-(9H-thioxanthene-9-ylidene)-piperidine derivatives wherein the nitrogen atom of the piperidine ring is bonded to an alkyl radical substituted with cyano, —COR or —COOR. Sleep-inducing properties are attributed to these derivatives.

Japanese patent JP 61106573 refers to the use of substituted 4-(9H-thioxanthene-9-ylidene)-piperidines as pesticides.

SUMMARY OF THE INVENTION

Accordingly, there is a need for a compound acting as selective 5-HT$_{2B}$ receptor antagonist.

In accordance with preferred embodiments, there is provided a compound according to the formula below:

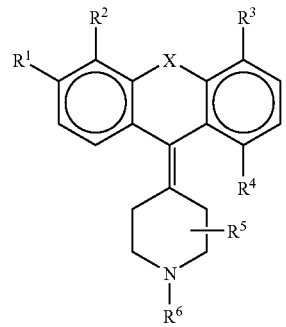

or a pharmaceutically acceptable salt thereof, wherein $R^1$ is methyl, ethyl, propyl, isopropyl, butyl, isobutyl, pentyl (straight or branched), hexyl (straight or branched), methoxy, ethoxy, propoxy, isopropoxy, butoxy, isobutoxy, phenoxy, trifluoromethyl, trifluoromethoxy, amino, dimethylamino, fluorine, chlorine, bromine, —CON(CH$_3$)$_2$ or CON(C$_2$H$_5$)$_2$; $R^2$ is methyl, ethyl, propyl, isopropyl, butyl, isobutyl, pentyl, hexyl, hydroxy or hydrogen, or R1 and R2 are forming a heterocycle; $R^3$ is methyl, ethyl, propyl, isopropyl, butyl isobutyl, pentyl, hexyl, hydroxy or hydrogen; $R^4$ is hydroxy, methoxy, ethoxy, propoxy, isopropoxy, butoxy, isobutoxy, trifluormethyl, amino, dimethylamino, diethylamino, fluorine, chlorine or bromine, methyl, ethyl, propyl, isopropyl, butyl or hydrogen; $R^5$ is methyl or hydrogen; $R^6$ is methyl or ethyl; and X is S, N or Se, with the proviso that if $R^1$ is ethoxy and X is S at least one of $R^2$, $R^3$, $R^4$ and $R^5$ is not hydrogen.

The residues $R^1$ and $R^4$ are of particular interest in the present invention. $R^1$ is involved in mediating the selectivity of the compound for the 5-HT$_{2B}$ receptor. $R^4$, however, is involved in mediating the affinity for the H$_1$ receptor. Preferably $R^1$ is a lower alkyl or alkoxy group, or halogenated alkyl or alkoxy group, sterically promoting, but not hindering the receptor binding. $R^4$ is preferably a polar group, particularly a small polar group, however, each group lowering the H1 affinity is suitable for the according use. $R^2$, $R^3$ and $R^5$ independently can be any residue, as long as the binding to the 5-$HT_{2B}$ receptor is not hindered.

The present invention is also directed to methods of using the compound shown above, or a pharmaceutical composition comprising said compound, for treatment of a disease state which can be alleviated by treatment with a 5-$HT_{2B}$ receptor antagonist.

The present invention further relates to a pharmaceutical composition comprising such a compound or a pharmaceutically acceptable salt thereof, in admixture with one or more pharmaceutically acceptable carriers.

Further the present invention is directed to the preparation of such compounds.

DETAILED DESCRIPTION OF THE PREFERRED EMBODIMENT

"Pharmaceutically acceptable salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, ascorbic acid and the like.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The term "disease state which can be alleviated by treatment with a 5-$HT_{2B}$ receptor antagonist" as used herein is intended to cover all disease states which are generally acknowledged in the art to be usefully treated with compounds having affinity for 5-$HT_{2B}$ receptors in general, and those disease states which have been found to be usefully treated by one of the compounds of the present invention. Such disease states include, but are not limited to, migraine, pain (e.g. acute, chronic, neuropathic, inflammatory and cancer pain) hypertension, disorders of the gastrointestinal tract (e.g., irritable bowel syndrome, hypertonic lower esophageal sphincter, motility disorders), restenosis, asthma and obstructive airway disease, prostatic hyperplasia (e.g., benign prostatic hyperplasia), and priapism.

In a preferred embodiment of the present invention the residues in the general formula shown above are as follows: $R^1$ is an isopropyl, dimethylamino, methoxy or ethoxy group, $R^2$ is methyl, ethyl or hydrogen, or $R^1$ and $R^2$ are forming a heterocycle, $R^3$ is ethyl or hydrogen, $R^4$ is methoxy, hydroxy, ethyl, methyl or hydrogen, $R^5$ is methyl or hydrogen, $R^6$ is methyl and X is S, N or Se, or a pharmaceutically acceptable salt thereof, with the proviso that if $R^1$ is ethoxy and X is S at least one of $R^2$, $R^3$, $R^4$ and $R^5$ is not hydrogen.

In a particularly preferred embodiment of the present invention the compound is selected of the group consisting of 4-(6-Isopropyl-1-methoxy-thioxanthen-9-yliden)-1-methyl-piperidine, 4-(6-Isopropyl-1-hydroxy-thioxanthen-9-yliden)-1-methyl-piperidine, 4-(6-Ethoxy-1-ethyl-thioxanthen-9-yliden)-1-methyl-piperidine, 4-(6-Ethoxy-1-methoxy-thiox-9-yliden)-1-methyl-piperidine, 4-(6-Ethoxy-1-hydroxy-thioxanthen-9-yliden)-1-methyl-piperidine, 4-(6-Methoxy-1-methoxy-thioxanthen-9-yliden)-1-methyl-piperidine, 4-(6-Dimethylamino-1-methoxy-thioxanthen-9-yliden)-1-methyl-piperidine, 4-(6-Dimethylamino-1-hydroxy-thioxanthen-9-yliden)-1-methyl-piperidine, 4-(3-Ethoxy-selenoxanthen-9-yliden)-1-methyl-piperidine, 4-(3-Ethoxy-1-methoxy-selenoxanthen-9-yliden)-1-methyl-piperidine, 4-(3-Ethoxy-1-hydroxy-selenoxanthen-9-yliden)-1-methyl-piperidine, 3-Ethoxy-9-(1-methyl-piperidine-4-ylidene)-9,10-dihydro-acridine, 6-Ethoxy-1-methoxy-9-( 1-methyl-piperidine-4-ylidene)-9,10-dihydro-acridine, 6-Ethoxy-1-hydroxy-9-(1-methyl-piperidine-4-ylidene)-9,10-dihydro-acridine, 4-(3-Ethoxy-5-ethyl-thioxanthen-9-yliden)-1-methyl-piperidine, 4-(3-Ethoxy-4-methyl-thioxanthen-9-yliden)-1-methyl-piperidine, 4-(3-Ethoxy-4-ethyl-thioxanthen-9-yliden)-1-methyl-piperidine, 4-(3-Ethoxy-thioxanthen-9-yliden)-1,3-dimethyl-piperidine, 4-(3,4-(Cyclopent-3'-oxy-1'-eno)-thioxanthen-9-yliden)-1-methyl-piperidine, 4-(3,4-(Cyclopent-4'-oxy-1'-eno)-thioxanthen-9-yliden)-1-methyl-piperidine and 4-(3,4-(Cyclopent-5'-oxy-1'-eno) -thioxanthen-9-yliden)-1-methyl-piperidine.

Although U.S. Pat. No. 3,275,640 describes the antihistaminic and/or antiserotonin properties of the class of substituted 1-hydrocarbyl-4-(9H-thioxanthene-9-ylidene)-piperidines in general it neither discloses the 4-(thio- or selenoxanthene-9-ylidene)-piperidine or acridine derivatives of the present invention nor correlates a selected derivative with a special antihistaminic and/or antiserotonin property. The term "antiserotonin property" is indeed a very broad term and refers to 14 different receptor subtypes. Even more U.S. Pat. No. 3,275,640 does not give any hint that a member of the class of substituted 1-hydrocarbyl-4-(9H-thioxanthene-9-ylidene)-piperidines has a selective affinity for one of the various 5-HT receptor subtypes, namely the human 5-$HT_{2B}$ receptor.

The property of the novel 4-(thio- or selenoxanthene-9-ylidene)-piperidine or acridine derivatives as a 5-$HT_{2B}$ receptor antagonist provides the possibility for a more specific treatment of the above-cited disease states and reduction of undesired side effects at the same time.

Gain of selectivity towards 5-$HT_{2B}$ receptors is accomplished via substitution at $R^1$. The remaining affinity to human Hi receptors is lowered by substitutions at $R^4$. The anti-histaminergic effects of non-$R^4$ substituted 4-(thio- or selenoxanthene-9-ylidene)-piperidine or acridine derivatives will likely result in sedation.

One general method for preparing substituted 1-hydrocarbyl-4-(10-thioxanthylidene)-piperidines—not including the novel compounds of the present invention—is described in U.S. Pat. No. 3,275,640.

The methods used to synthesis the novel compounds is as follows: A "top" ketone 1 was reacted with a "bottom" Grignard reagent 2 to produce the coupled alcohol 3. The alcohol 3 was dehydrated with formic acid or other acid to produce the desired alkene 4.

Scheme I:

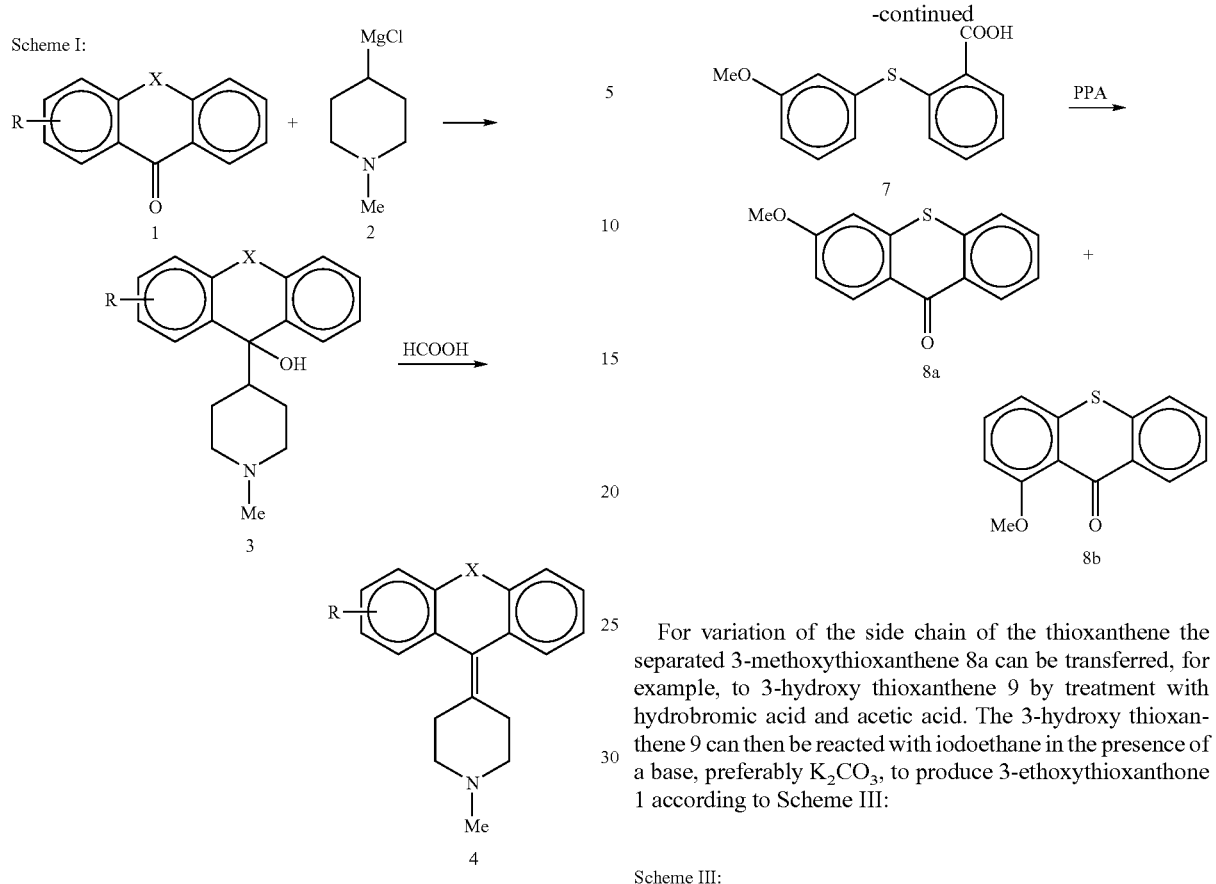

One way to synthesize the educt 1, i.e. 3-ethoxythioxanthone, starts from 3-methoxythioxanthone 8a that may be prepared by a procedure described by I. Cervena et al. 1978 *Coll Czech Chem Comm* 41:881-904 (Scheme II). 3-Methoxythiophenol 5 is reacted with 2-iodobenzoic acid 6 in a boiling solution of KOH in the presence of copper. After addition of hydrochloric acid the coupled acid 7 is obtained. The acid 7 is cyclized with polyphosphoric acid to produce a mixture of the isomers 3-methoxythioxanthone 8a and 1-methoxythioxanthone 8b that can be separated by chromatography, preferably column chromatography. Other separation technologies may be used on an industrial scale to manufacture and separate the product, including, but not limited to, for example, Simulated Moving Bed Separations, Capillary Electrophoresis, High Throughput High Pressure Multi or Single Column Separation methods using chiral or non chiral support and separations media. Enzymatic dehydration in combination with any of the aforementioned technologies or enzyme enrichment separation methods used separately or in combination with any above can also be used.

Scheme II:

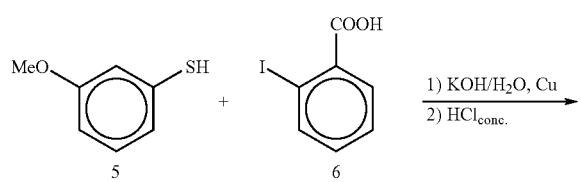

For variation of the side chain of the thioxanthene the separated 3-methoxythioxanthene 8a can be transferred, for example, to 3-hydroxy thioxanthene 9 by treatment with hydrobromic acid and acetic acid. The 3-hydroxy thioxanthene 9 can then be reacted with iodoethane in the presence of a base, preferably K$_2$CO$_3$, to produce 3-ethoxythioxanthone 1 according to Scheme III:

Scheme III:

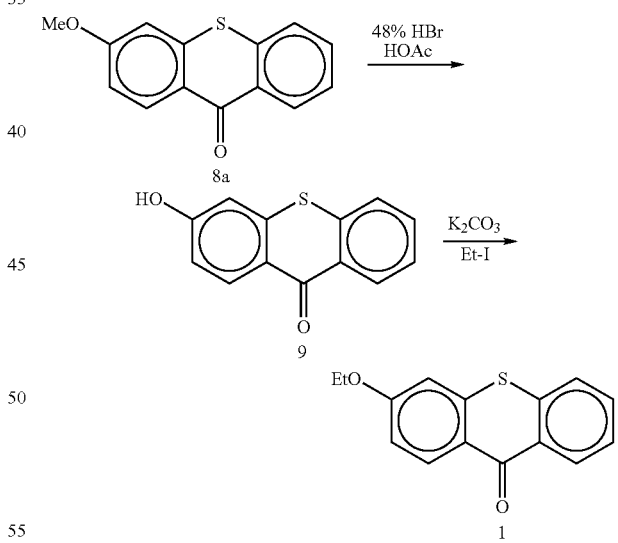

The other derivatives like 4-(6-Isopropyl-1-methoxy-thioxanthen-9-yliden)-1-methyl-piperidine, 4-(6-Isopropyl-1-hydroxy-thioxanthen-9-yliden)-1-methyl-piperidine, 4-(6-Ethoxy-1-ethyl-thioxanthen-9-yliden)-1-methyl-piperidine, 4-(6-Ethoxy-1-methoxy-thioxanthen-9-yliden)-1-methyl-piperidine, 4-(6-Ethoxy-1-hydroxy-thioxanthen-9-yliden)-1-methyl-piperidine, 4-(6-Dimethylamino-1-methoxy-thioxanthen-9-yliden)-1-methyl-piperidine, 4-(6-Dimethylamino-1-hydroxy-thioxanthen-9-yliden)-1-methyl-piperidine, 4-(3-Ethoxy-selenoxanthen-9-yliden)-1-methyl-piperidine, 4-(3-

Ethoxy-1-methoxy-selenoxanthen-9-yliden)-1-methyl-piperidine, 4-(3-Ethoxy-1-hydroxy-selenoxanthen-9-yliden)-1-methyl-piperidine, 3-Ethoxy-9-(1-methyl-piperidine-4-ylidene)-9,10-dihydro-acridine, 6-Ethoxy-1-methoxy-9-(1-methyl-piperidine-4-ylidene)-9,10-dihydro-acridine, 6-Ethoxy-1-hydroxy-9-(1-methyl-piperidine-4-ylidene)-9,10-dihydro-acridine, 4-(3-Ethoxy-5-ethyl-thioxanthen-9-yliden)-1-methyl-piperidine, 4-(3-Ethoxy-4-methyl-thioxanthen-9-yliden)-1-methyl-piperidine, 4-(3-Ethoxy-4-ethyl-thioxanthen-9-yliden)-1-methyl-piperidine and 4-(3-Ethoxy-thioxanthen-9-yliden)-1,3-dimethyl-piperidine, 4-(3,4-(Cyclopent-3'-oxy-1'-eno)-thioxanthen-9-yliden)-1-methyl-piperidine, 4-(3,4-(Cyclopent-4'-oxy-1'-eno)-thioxanthen-9-yliden)-1-methyl-piperidine and 4-(3,4-(Cyclopent-5'-oxy-1'-eno)-thioxanthen-9-yliden)-1-methyl-piperidine may be synthesized accordingly based on the method of Cervenà, I. et al. as described in Cervenà, I. et al. 1978 *Collection Czechoslov Chem Cumm* 41:881-904 or by one of the methods of Watanabe, M. et al. as described in: Watanabe M. et al. 1984 *Chem Pharm Bull* 32:1264-1267; Watanabe M. et al. 1986 *Chem Pharm Bull* 34:2810-2820; and Watanabe, M. et al. 1989 *Chem Pharm Bull* 37:36-41.

The compounds of this invention are human $5\text{-}HT_{2B}$ receptor antagonists. Affinity for the $5\text{-}HT_{2B}$ receptors was demonstrated using an in vitro binding assay utilizing cloned human $5\text{-}HT_{2B}$ receptors radiolabeled with [$^3$H]-5HT, as shown in the examples. Selectivity for the human $5\text{-}HT_{2B}$ receptor was shown by counter screening at human $5\text{-}HT_{2A}$ and $5\text{-}HT_{2C}$ receptors. Antagonist properties for $HT_{2B}$ were determined in rat stomach fundus longitudinal muscle. Affinity for the human H1 receptor was determined using an in vitro binding assay utilizing cloned human HI receptors radiolabeled with [$^3$H]-mepyramine, as shown in the examples. Antagonist properties were determined by [$^3$H] Inositol phosphate production in transiently transfected HEK-293 cells.

Accordingly, the compounds of this invention are useful for treating diseases which can be ameliorated by blockade of $5\text{-}HT_{2B}$ receptors. Because of the similarities in the pharmacology of ligand interactions at $5\text{-}HT_{2C}$ and $5\text{-}HT_{2B}$ receptors many of the therapeutic targets that have been proposed for $5\text{-}HT_{2C}$ receptor antagonists are also targets for $5\text{-}HT_{2B}$ receptor antagonists. In particular, several clinical observations suggest a therapeutic role for $5\text{-}HT_{2B}$ receptor antagonists in the prevention of migraine, in that mobilization of 5-HT into the plasma is believed to be a precipitating factor in migraine. Additionally, non-selective $5\text{-}HT_{2B}$ receptor agonists provoke migraine attacks in susceptible individuals, and non-selective $5\text{-}HT_{2B}$ receptor antagonists are effective in preventing the onset of migraine (Kalkman 1994 *Life Sciences* 54:641-644). It is speculated that activation of $5\text{-}HT_{2B}$ receptors located on endothelial cells of meningeal blood vessels triggers migraine attacks through the formation of nitric oxide (Schmuck et al. 1996 *Eur J Neurosci* 8:959-967).

Experimental evidence indicates that the compound of the present invention are useful in the treatment of pain, including acute, chronic, neuropathic, inflammatory, and cancer pain, particularly inflammatory pain. 5-HT (serotonin) plays a key role in the regulation of transmission of nociceptive information at various levels of the peripheral and central nervous systems (see Richardson B. P. 1990 *Ann NY Acad Sci* 600: 511-520). Moreover, neuronal systems containing 5-HT are involved not only in the regulation of nociceptive input at the spinal and supraspinal level, but in mediating the nociceptive action of other analgesics including the opiates. 5-HT is a mediator of sensitization of nerve terminal nociceptors that may occur in the genesis of pain associated with inflammation. The $5\text{-}HT_{2B}$ receptor is highly sensitive to activation by 5-HT and specific blockade by selective $5\text{-}HT_{2B}$ antagonists may provide a novel avenue toward analgesia therapy.

Experimental evidence supports a therapeutic role for $5\text{-}HT_{2B}$ receptor antagonists in treating hypertension. In hypertension, one of the most profound increases in vascular responsiveness is observed for serotonin. Two lines of evidence imply that this results from a switch in the receptor mediating vasoconstriction from predominantly $5\text{-}HT_{2A}$ to predominantly $5\text{-}HT_{2B}$. First, serotonin induced contractions of isolated blood vessels from hypertensive animals become resistant to block by selective $5\text{-}HT_{2A}$ receptor antagonists, but remain sensitive to non-selective $5\text{-}HT_{2B}$ receptor antagonists. Second, there is an increase in $5\text{-}HT_{2B}$ receptor mRNA in vessels from hypertensive animals (Watts et al. 1996 *J Pharmacol Exp Ther* 277:1103-13; and Watts et al. 1995 *Hypertension* 26:1056-1059). This hypertension-induced shift in the population of receptor subtype mediating constrictor responses to 5-HT suggests that selective block of vasoconstrictor $5\text{-}HT_{2B}$ receptors may be of therapeutic benefit in the treatment of hypertension.

Clinical and experimental evidence supports a therapeutic role for $5\text{-}HT_{2B}$ receptor antagonists in treating disorders of the gastrointestinal tract, in particular irritable bowel syndrome (IBS). Although the pathology underlying ][BS remains unclear, there is a well-established implied role for the involvement of serotonin. Thus, meals with a high serotonin content can exacerbate symptoms in some patients (Lessorf 1985 *Scand J Gastroenterology* 109:117-121), while in pre-clinical studies, serotonin has been shown directly to sensitize visceral sensory neurons resulting in an enhanced pain response similar to that observed in IBS (Christian et al. 1989 *J Applied Physiol* 67:584-591; Sanger et al. 1996 *Neurogastroenterology and Motility* 8:319-331). The possibility that $5\text{-}HT_{2B}$ receptors play a crucial role in the sensitizing actions of serotonin are suggested by several lines of evidence. Firstly, $5\text{-}HT_{2B}$ receptors are present in the human intestine (Borman et al. 1995 *Brit J Pharmacol* 114:1525-1527; Borman et al. 1997 *Ann of the New York Acad of Sciences* 812:222-223). Secondly, activation of $5\text{-}HT_{2B}$ receptors can result in the production of nitric oxide, an agent capable of sensitizing sensory nerve fibers (Glusa et al. 1993 *Naunyn-Schmied Arch Pharmacol* 347:471-477; Glusa et al. 1996 *Brit J Pharmacol* 119:330-334). Thirdly, poorly selective drugs which display high affinity for the $5\text{-}HT_{2B}$ receptor are clinically effective in reducing the pain associated with IBS and related disorders (Symon et al. 1995 *Arch Disease in Childhood* 72:48-50; Tanum et al. 1996 *Scand J Gastroenterol* 31:318-325). Together these findings suggest that a selective $5\text{-}HT_{2B}$ receptor antagonist will attenuate both the gastrointestinal pain and abnormal motility associated with IBS.

Clinical and experimental evidence supports a therapeutic role for $5\text{-}HT_{2B}$ receptor antagonists in treating restenosis. Angioplasty and bypass grafting are associated with restenosis which limits the efficacy of these procedures. Platelet-rich thrombus formation is the predominant cause of acute occlusion whereas serotonin, among other platelet-derived mediators, is thought to contribute to late restenosis (Barradas et al. 1994 *Clinica Chim Acta* 230:157-167). This late restenosis involves proliferation of the vascular smooth muscle. Two lines of evidence implicate a role for $5\text{-}HT_{2B}$ receptors in this process. Firstly, serotonin displays a potent mitogenic activity in cultured smooth muscle and endothelial cells via activation of $5\text{-}HT_2$ receptors (Pakala et al, 1994 *Circulation* 90:1919-1926). Secondly, this mitogenic activity appears to be mediated via activation of a tyrosine kinase second messenger pathway involving mitogen activated protein kinase (MAPK) (Lee et al. 1997 *Am J Physiol* 272(1 pt 1):C223-230; Kelleher et al. 1995 *Am J Physiol* 268(6 pt 1):L894-901). The recent demonstration that 5-HT$_{2B}$ receptors couple to MAPK (Nebigil et al. 2000 *PNAS USA* 97:22591-2596), coupled with the high affinity of serotonin for this receptor subtype, indicates that a selective 5-HT$_{2B}$ receptor antagonist may offer protection against restenosis of autografted blood vessels or of vessels following angioplasty.

Clinical and experimental evidence supports a therapeutic role for 5-HT$_{2B}$ receptor antagonists in treating asthma and obstructive airway disease. Abnormal proliferation of airways smooth muscle, together with hyper-reactivity of the smooth muscle to constrictor stimuli including serotonin, plays a significant role in the pathogenesis of human airway disease such as asthma and bronchial pulmonary dysplasia (James et al. 1989 *Am Review of Respiratory Disease* 139: 242-246; Margraf et al. 1991 *Am Review of Respiratory Disease* 143:391-400). In addition to other subtypes of serotonin receptor, 5-HT$_{2B}$ receptors are present in bronchial smooth muscle (Choi et al. 1996 *FEBS Lett* 391:45-51) and have been shown to stimulate smooth muscle mitogenesis in airways smooth muscle (Lee et al. 1994 *Am J Physiol* 266:L46-52). Since elevated concentrations of circulating free serotonin are closely associated with clinical severity and pulmonary function in symptomatic asthmatics, serotonin may play an important role in the pathophysiology of acute attacks (Lechin et al. 1996 *Ann Allergy Asthma Immunol* 77:245-253). These data suggest that an antagonist of 5-HT2B receptors in airways smooth muscle may therefore be useful in preventing airways constriction resulting from the elevated levels of circulating serotonin and prevent proliferation of the airways smooth muscle that contributes to the long-term pathology of this disease.

Experimental evidence supports a therapeutic role for 5-HT$_{2B}$ receptor antagonists in treating prostatic hyperplasia. Obstruction of the urinary tract can occur as a result of prostatic hyperplasia and excessive prostatic constriction of the urethra. This in turn leads to diminished urinary flow rates and an increased urgency and frequency of urination. 5-HT$_{2B}$ receptors are present in the human prostate (Kursar et al. 1994 *Mol Pharmacol* 46:227-234) and a receptor with the pharmacological attributes of this receptor subtype mediates contraction of the tissue (Killam et al. 1995 *Eur J Pharmacol* 273: 7-14). Some drugs effective in the treatment of benign prostatic hyperplasia block 5-HT mediated contractions of the prostate (Noble et al. 1997 *Brit J Pharmacol* 120:231-238). 5-HT$_{2B}$ receptors mediate smooth muscle and fibrotic hyperplasia (Launay et al. 1996 *J Biol Chem* 271:3141-3147) and serotonin is mitogenic in the prostate (Cockett et al. 1993 *Urology* 43:512-519), therefore a selective 5-HT$_{2B}$ receptor antagonist may have utility not only in mitigating the excessive prostatic constriction, but also in preventing progression of tissue hyperplasia.

Experimental evidence supports a therapeutic role for 5-HT$_{2C}$ receptor antagonists in treating priapism (Kennett 1993 *Curr Opin Invest Drugs* 2:317-362). MCPP produces penile erections in rats, which effect is blocked by non-selective 5-HT$_{2C/2A/2B}$ receptor antagonists but not by selective 5-HT$_{2A}$ receptor antagonists (Hoyer 1989 *Peripheral actions of 5-HT* Fozard J. ed., Oxford University Press, Oxford, 72-99). This therapeutic target for 5-HT$_{2C}$ receptor antagonists is equally a target for 5-HT$_{2B}$ receptor antagonists.

In applying the compounds of this invention to treatment of the above conditions, administration of the active compound and salts described herein can be via any of the accepted modes of administration, including oral, parenteral and otherwise systemic route of administration. Any pharmaceutically acceptable mode of administration can be used, including solid, semi-solid or liquid dosage forms, such as, for example, tablets, suppositories, pills, capsules, powders, liquids, suspensions, or the like, preferably in unit dosage forms suitable for single administration of precise dosages, or in sustained or controlled release dosage forms for the prolonged administration of the compound at a predetermined rate. The compositions will typically include a conventional pharmaceutical carrier or excipient and at least one of the compounds of the present invention or the pharmaceutically acceptable salts thereof and, in addition, may include other medicinal agents, pharmaceutical agents, carriers, adjuvants, etc.

The amount of one of the derivatives of the present invention administered will of course, be dependent on the subject being treated, the severity of the affliction, the manner of administration and the judgment of the prescribing physician. However, an effective dose for oral, parenteral and otherwise systemic routes of administration is in the range of 0.01-20 mg/kg/day, preferably 0.1-10 mg/kg/day. For an average 70 kg human, this would amount to 0.7-1400 mg per day, or preferably 7-700 mg/day.

One of ordinary skill in the art of treating such diseases will be able, without undue experimentation and in reliance upon personal knowledge and the disclosure of this application, to ascertain a therapeutically effective amount of one of the inventive piperidine compounds for a given disease.

For solid compositions, conventional non-toxic solid carriers include, for example, pharmaceutical grades of mannitol, lactose, cellulose, cellulose derivatives, sodium crosscarmellose, starch, magnesium stearate, sodium saccharin, talcum, glucose, sucrose, magnesium carbonate, and the like may be used. The active compound as defined above may be formulated as suppositories using, for example, polyalkylene glycols, e.g., PEG (polyethyleneglycol) or PEG derivatives, acetylated triglycerides and the like, as the carrier. Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. The composition or formulation to be administered will, in any event, contain a quantity of the active compound(s) in an amount effective to alleviate the symptoms of the subject being treated.

Dosage forms or compositions containing one of the present piperidine compounds in the range of 0.25 to 95% by weight with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, cellulose, cellulose derivatives, sodium crosscarmellose, starch, magnesium stearate, sodium saccharin, talcum, glucose, sucrose, magnesium, carbonate, and the like. Such compositions take the form of solutions, suspensions, tablets, pills, capsules, powders, sustained release formulations and the like. Such compositions may contain 1 to 95% by weight of one of the compounds of the present invention, more preferably 2 to 50% by weight, most preferably 5 to 8% by weight.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, triethanolamine sodium acetate, etc.

Transdermal or "pulsed" transdermal administration may be supported by cremes, gels, dispersions and the like.

A more recently devised approach for parenteral administration employs the implantation of a slow-release or sustained-release system, such that a constant level of dosage is maintained (see, e.g., U.S. Pat. No. 3,710,795).

The percentage of active compounds contained in such parental compositions is highly dependent on the specific nature thereof, as well as the activity of the compound and the needs of the subject. However, percentages of one of the inventive piperidine compounds of 0.1 to 10% by weight in solution are employable, and will be higher if the composition is a solid which will be subsequently diluted to the above percentages. Preferably the composition will comprise 0.2 to 2% by weight of one of the piperidine compounds in solution.

In applying the compounds of the invention to treatment of diseases or disorders of the eye which are associated with an abnormally high intraocular pressure, administration may be achieved by any pharmaceutically acceptable mode of administration which provides adequate local concentrations to provide the desired response. These include direct administration to the eye via drops and controlled release inserts or implants, as well as systemic administration as previously described.

Drops and solutions applied directly to the eye are typically sterilized aqueous solutions containing 0.1 to 10% by weight, most preferably 0.5 to 1% by weight of one of the novel piperidine compounds, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6-8. Typical preservatives are phenyl mercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by dissolving the solutes in a suitable quantity of water, adjusting the pH to about 6.8-8.0, making a final volume adjustment with additional water, and sterilizing the preparation using methods known to those in the art.

The dosage level of the resulting composition will, of course, depend on the concentration of the drops, the condition of the subject and the individual magnitude of responses to treatment. However, a typical ocular composition could be administered at the rate of about 2-10 drops per day per eye of a 0.5% by weight solution of one of the piperidine compounds.

The compositions of the present invention may also be formulated for administration in any convenient way by analogy with other topical compositions adapted for use in mammals. These compositions may be presented for use in any conventional manner with the aid of any of a wide variety of pharmaceutical carriers or vehicles. For such topical administration, a pharmaceutically acceptable non-toxic formulation can take the form of semisolid, liquid, or solid, such as, for example, gels, creams, lotions, solutions, suspensions, ointments, powders, or the like. As an example, the active component may be formulated into a syrup or gel using ethanol, propylene glycol, propylene carbonate, polyethylene glycols, diisopropyl adipate, glycerol, water, etc., with appropriate gelling agents, such as Carbomers, Klucels, etc. If desired, the formulation may also contain minor amounts of non-toxic auxiliary substances such as preservatives, antioxidants, pH buffering agents, surface active agents, and the like. Actual methods of preparing such dosage forms are known, or will be apparent, to those skilled in the art; for example, see Remington's Pharmaceutical Sciences, Mack Publishing Company, Easton, Pa., 19th Edition, 1995.

Preferably the pharmaceutical composition is administered in a single unit dosage form for continuous treatment or in a single unit dosage form ad libitum when relief of symptoms is specifically required.

EXAMPLE 1

6-Ethoxy-1-methoxythioxanthone 1 is reacted with the Grignard reagent 2 prepared from 1-methyl-4-halopiperidine, preferably 1-methyl-4-chloropiperidine, according to Scheme I. The alcohol 3 is isolated and dehydrated with an acid, preferably hydrochloric acid or formic acid to produce 1-methyl-4-(3-ethoxy-9H-thioxanthene-9-ylidene)-piperidine (4).

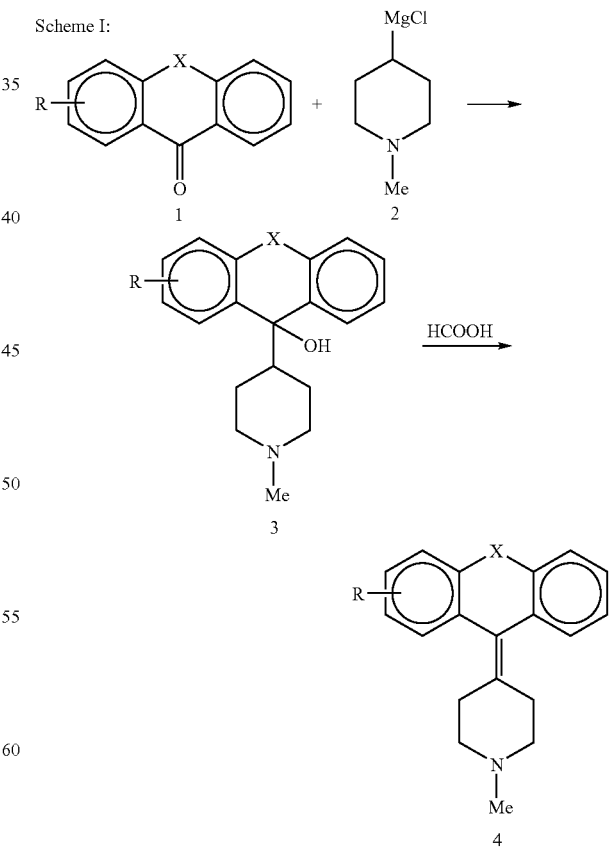

Scheme I:

One way to synthesize the 6-ethoxy-1-methoxythioxanthone 1 is described by I. Cervena et al. 1978 Coll Czech Chem Comm 41:881-904 (Scheme II). 3-Ethoxythiol 5 is reacted with 2-iodo-4-methoxybenzoic acid 6 in a boiling aqueous solution of KOH in the presence of copper. After addition of hydrochloric acid the coupled acid 7 is obtained. The acid 7 is cyclized with polyphosphoric acid to produce a mixture of the isomeres 1-methoxy-6-ethoxythioxanthone 8a and 1-methoxy-8-ethoxythioxanthone 8b that can be separated by chromatography, preferably column chromatography.

Scheme II:

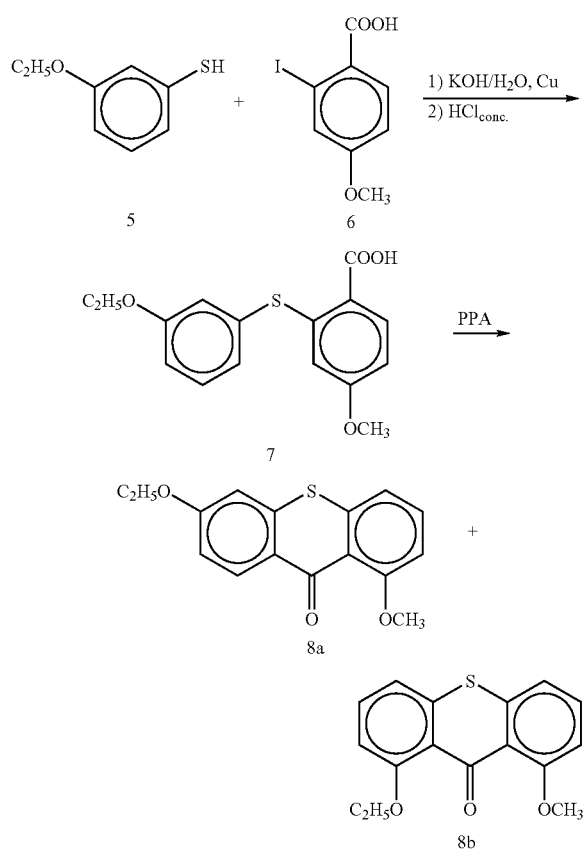

A second procedure to produce the "top" ketone is based on the method of M. Watanabe et al. 1989 *Chem Pharm Bull* 37:36-41. Starting from 4-isopropylbenzoic acid 10, this is converted to the amide 11 which is treated with strong base to extract the proton adjacent to the amide group and, after the introduction of molecular sulfur and treatment with acid, the thiol group is introduced as in 12. Treatment of the bromoanisole 13 with strong base converts it to a benzyne that reacts with 12 to produce the desired ketone 14.

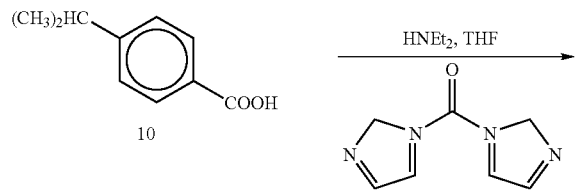

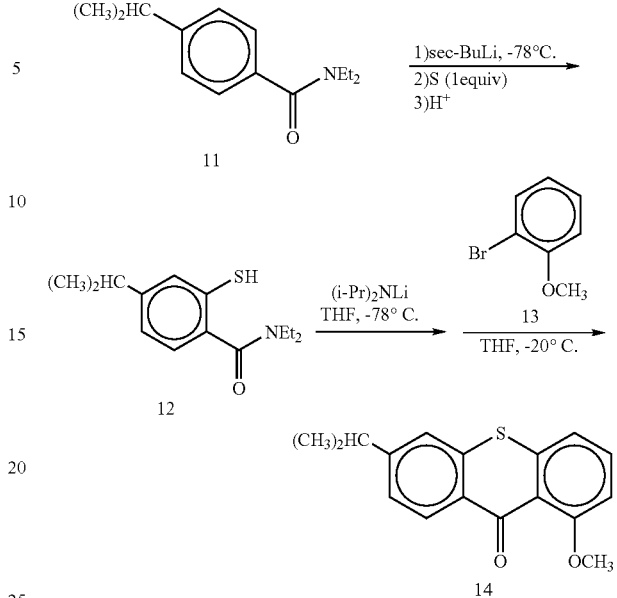

Which procedure is suitable for the different compounds of the present invention depends particularly on the availability of the starting materials.

EXAMPLE 2

Single steps of the preparation of 5 compounds: 4-(6-Ethoxy-1-methoxy-thioxanthen-9-yliden)-1-methyl-piperidine, 4-(6-Isopropyl-1-methoxy-thioxanthen-9-yliden)-1-methyl-piperidine, 4-(6-Ethoxy-1-ethyl-thioxanthen-9-yliden)-1-methyl-piperidine, 4-(3-Ethoxy-selenoxanthen-9-yliden)-1-methyl-piperidine, 3-Ethoxy-9-(1-methyl-piperidine-4-ylidene)-9,10-dihydro-acridine.

All reactions described in the following chapters must be performed under protecting atmosphere (dry argon or dry $N_2$). Analysis are done with HPLC-MS-coupling (214 nm, ESI positive mode, +30 V). Extraction steps of the thiols should be done with degassed or argon flushed solvents to prevent reoxidation to the disulfide.

2.1 Synthesis of the thioxanthenes/selenoxanthene 2.1.1 Synthesis of 4-Ethoxy-benzoic acid-diethylamide 4-Ethoxybenzoic acid (20.0 g, 120 mmol) is dissolved in thionyl chloride (14 ml) and refluxed for 3 hours. After cooling down the reaction mixture to room temperature, the excess thionyl chloride is evaporated. The resulting crude acid chloride is immediately dissolved in dry DCM (125 ml) and the solution is cooled with ice water. 125 ml of diethyl amine is added drop wise. After addition of the amine, the reaction mixture is allowed to warm up to room temperature. After stirring the mixture at room temperature over night (16 h), the solution is washed with 1.0 N hydrochloric acid (3×100 ml), saturated $NaHCO_3$-solution (3×100 ml) and brine (3×100 ml). The organic layer is dried with $Na_2SO_4$, filtered off and evaporated to dryness.

| | |
|---|---|
| Purity: | 98%; |
| Yield: | 25 g, 94% |

2.1.2 Synthesis of 4-Isopropyl-benzoic acid-diethylamide

4-Isoporpylbenzoic acid (5 g, 30.5 mmol) is dissolved in thionyl chloride (10 ml) and refluxed for 3 hours. After cooling down the reaction mixture to room temperature, the excess thionyl chloride is evaporated. The crude acid chloride is immediately dissolved in dry DCM (50 ml) and the solution is cooled with ice water. Dienthyl amine (32 ml, 0.3 mol) is added drop wise. After addition of the amine, the reaction mixture is allowed to warm up to room temperature. After stirring the mixture at room temperature over night (12-14 h), the solution is washed with 1.0 N hydrochloric acid (3×50 ml), saturated NaHCO$_3$-solution (3×50 ml) and brine (3×50 ml). The organic layer is dried with Na$_2$SO$_4$, filtered off and evaporated to dryness.

| | |
|---|---|
| Purity: | 96%; |
| Yield: | 6.0 g, 90% |

2.1.3 Synthesis of 4-Ethoxy-2-thiobenzoic acid-diethylamide

4-Ethoxy-benzoic-acid-diethylamide (4.43 g, 20 mmol) and N,N,N, N-Tetramethylethylendiamin (5.1 ml, 23.8 mmol) are dissolved in dry THF (100 ml). The solution is cooled to −78° C. Then sec. buthyl lithium (1.3 M in n-Hexan/THF, 13.73 ml, 23.8 mmol) is added drop wise, so that the temperature never exceeds −70° C. The solution is stirred at −78° C for 1 h, then powdered sulfur (1.36 g, 40 mmol) is added in one step.

The cool bath is removed and the solution is allowed to warm up to room temperature and is stirred over night (16 h). Saturated NH$_4$Cl-solution (100 ml) and then 10% aqueous HCl (50 ml) are added. The mixture is evaporated to dryness. The residue is extracted with methylene chloride (100 ml), dried with Na$_2$SO$_4$, filtered off and the solvent is evaporated.

The crude product is dissolved in acetic acid (100 ml). Water (100 ml) and zinc (5 g) is added and the mixture is stirred with a magnetic stirrer and heated at 65° C. for 24 h. The solution is extracted with methylene chloride (1×100 ml). The organic layer is separated and washed with water (3×100 ml). The solvent is then removed. The crude product is purified with an ISCO-flash system using methylene chloride and methanol (gradient).

| | |
|---|---|
| Purity: | 75%; |
| Yield: | 3.5 g, 70% |

2.1.4 Synthesis of 4-Isopropyl-2-thiobenzoicacid-diethylamide

4-Isopropylbenzoic acid diethylamide (2.19 g, 10 mmol) and N,N,N, N-Tetramethylethylendiamin (2.6 ml, 11.9 mmol) are dissolved in dry THF (33 ml). The solution is cooled down to −78° C. Then sec. buthyl lithium (1.3 M in n-Hexan/THF, 9.15 ml, 11.9 mmol) is added drop wise, so that the temperature never exceeded −70° C. The solution is stirred 1 h at −78° C., then powdered sulfur (0.64 g, 30 mmol) is added in one step.

The cool bath is removed and the solution is allowed to warm up to room temperature and is stirred over night (16 h). Saturated NH$_4$Cl-solution (100 ml) and then 10% aqueous HCl (50 ml) are added. The mixture is evaporated to dryness. The residue is extracted with methylene chloride (100 ml), dried with Na$_2$SO$_4$, filtered off and the solvent is evaporated.

The crude product is dissolved in acetic acid (50 ml). Water (50 ml) and zinc (2.5 g) is added and the mixture is stirred with a magnetic stirrer and heated at 65° C. for 24 h. The solution is extracted with methylene chloride (1×100 ml). The organic layer is separated and washed with water (3×100 ml) and brine (1×100 ml). The solution is dried with Na$_2$SO$_4$ and then filtered off. The solvent is then removed. The crude product is purified with an ISCO-flash system using methylene chloride and methanol (gradient).

| | |
|---|---|
| Purity: | 76%; |
| Yield: | 950 mg, 38% |

2.1.5 Synthesis of Di-[4-Ethoxy-N,N-diethyl-2-seleno-benzamide]

4-Ethoxybenzoic acid diethylamide (1.32 g, 6 mmol) and N,N,N, N-Tetramethylethylendiamin (1.63 ml, 7.6 mmol) are dissolved in dry THF (40 ml). The solution is cooled down to −78° C. Then sec. buthyl lithium (1.3 M in n-Hexan/THF, 5.85 ml, 7.6 mmol) is added drop wise, so that the temperature never exceeded −70° C. The solution is stirred 1 h at −78° C., then powdered selen (0.95 g, 12 mmol) is added in one portion.

The cool bath is removed and the solution is allowed to warm up to room temperature and is stirred over night (16 h). Saturated NH$_4$Cl-solution (100 ml) and then 10% aqueous HCl (50 ml) are added. The mixture is evaporated to dryness. The residue is extracted with methylene chloride (100 ml), dried with Na$_2$SO$_4$, filtered off and the solvent is evaporated.

The crude product is dissolved in acetic acid (50 ml). Water (25 ml) and zinc (2.5 g) is added and the mixture is stirred with a magnetic stirrer and heated at 65° C. for 24 h. The solution is extracted with methylene chloride (1×100 ml). The organic layer is separated and washed with water (3×100 ml) and brine (1×100 ml). The solution is dried with Na$_2$SO$_4$ and then filtered off. The solvent is then removed. The purity of the crude product was high so no further purification was necessary.

| | |
|---|---|
| Purity: | 93%; |
| Yield: | 1.05 g, 58% |

2.1.6 Synthesis of 6-Ethoxy-1-methoxy-thioxanthen-9-one

4-Ethoxy-2-thiobenzoicacid-diethylamide (1 g, 6.98 mmol) is dissolved in dry THF (105 ml) and cooled to −78° C. LDA (Lithium-diisopropyl amide, 1 M solution, 27.92 ml, 13.96 mmol) is added drop wise. The solution is stirred for one hour at −78° C. The solution is allowed to warm up to −20° C. and 2-methoxybromobenzene (2.176 ml, 17.45 mmol in 30 ml dry THF) is added to the solution drop wise. The solution is allowed to warm up to room temperature and stirred over night (16 h).

Saturated $NH_4Cl$-solution (50 ml) and then 10% HCl-solution (50 ml) is added to the reaction solution. The mixture is evaporated to dryness and the residue is extracted with $CH_2Cl_2$ (150 ml). The organic solvent is washed 3× with brine (100 ml), dried with $Na_2SO_4$, filtered off and the solvent is evaporated. The crude product is purified twice by flash-chromatography (CH2Cl2/methanol gradient).

| | |
|---|---|
| Purity (HPLC, 214 nm): | 84.4%, |
| Yield: | 0.5 g (25%) |

2.1.7 Synthesis of 6-Ethoxy-1-ethyl-thioxanthen-9-one

The synthesis is done according to step 2.1.6, using 2-ethylbromobenzene instead of 2-methoxybromobenzene.

Purification of the crude product is done once by flash-chromatography.

| | |
|---|---|
| Purity (HPLC, 214 nm): | 86%; |
| Yield: | 220 mg, 10%. |

2.1.8 Synthesis of 6-Isopropyl-1-methoxy-thioxanthen-9-one

The synthesis is done according to step 2.1.6, using 4-Isopropyl-2-thiobenzoicacid-diethylamide (0.9 g, 6.32 mmol) as educt.

Purification of the crude product is done once by flash-chromatography.

| | |
|---|---|
| Purity (HPLC, 214 nm): | 79%, |
| Yield: | 250 mg, 14%. |

2.1.9 Synthesis of 3-Ethoxyselenoxanthene-9-one

The synthesis is done according to step 2.1.6, using the diselenide obtained from step 2.1.5 (1.0 g, 4.3 mmol selenide) as educt and bromobenzene (1.146 ml, 10.9 mmol) as reactant.

Purification of the crude product is done once by flash-chromatography.

| | |
|---|---|
| Purity (HPLC, 214 nm): | 86%, |
| Yield: | 300 mg, 22%. |

2.2 Synthesis of the final compounds 4-(6-Ethoxy-1-methoxy-thioxanthen-9-yliden -1-methyl-piperidine, 4-(6-Isopropyl-1-methoxy-thioxanthen-9-yliden)-1-methyl-piperidine, 4-(6-Ethoxy-1-ethyl-thioxanthen-9-yliden)-1-methyl-piperidine, 4-(3-Ethoxy-selenoxanthen-9-yliden)-1-methyl-piperidine

2.2.1 Synthesis of the Grignard-reagent 1-methyl-piperidine-4-yl-magnesium chloride 4-Chlor-1-methylpiperidine*HCl (20 g) is converted into its free amine by dissolving it in 25% $NH_3/H_2O$-solution (250 ml), followed by extraction with ether. The organic layer is washed twice with brine, dried with $Na_2SO_4$ and evaporated. The pure amine is kept under argon.

2 g Amine (ca. 15 mmol) is dissolved in dry THF (7 ml). To magnesium pellets (0.434 g, 16.5 mmol) and dry THF (1.4 ml), one crystal of iodine and ethyl iodide (60.4 μl, 0.75 μmol) are added. As soon as the Grignard reaction starts, the amine solution is added drop wise to the solution. The solution is slightly stirred and sometimes heated with a heat-gun to keep the THF boiling. After the amine solution is added, the reaction solution is refluxed for 2 h to finish the reaction.

The solution must be kept under argon.

2.2.2 Synthesis of 4-(6-Ethoxy-1-methoxy-thioxanthen-9-ylidene)-1-methyl-piperidine 6-Ethoxy-1-methoxy-thioxanthene-9-one (100 mg, 0.349 mmol) is dissolved in dry THF (5 ml). 1-Methyl-piperidine-4-yl-magnesium chloride (3 eq, from step 2.2.1) is added drop wise. After completion of the addition of the Grignard reagent, the solution is allowed to stir over night. Control of the reaction is done by TCL (1% methanol/$CH_2Cl_2$). After the reaction is complete, the reaction is quenched first with acetic acid (5 ml), then with water (5 ml). The solvents are evaporated and the resulting carbinol is dehydrated with acetic anhydride (5 ml, reflux, 4 h).

The acetic anhydride is evaporated and the residue is dissolved in 1 N KOH-solution (5 ml). The free amine is extracted once with methylene chloride (10 ml). The solution is dried with $Na_2SO_4$ and the solvent is evaporated.

The crude product is purified with flash chromatography and then transferred into its hydrochloride by heating it in aqueous HCl (50 eq HCl, 5 ml, 4 h, 50° C.). The solvent is evaporated and the product dissolved in a mixture of tert. butyl alcohol and water (2 ml, 4:1, v/v) and lyophilized.

| | |
|---|---|
| Purity: | 92% |
| Yield: | 20 mg, 16% |

2.2.3 Synthesis of 4-(6-Isopropyl-1-methoxy-thioxanthen-9-ylidene)-1-methyl-piperidine 6-Isopropyl-1-methoxy-thioxanthene-9-one (100 mg, 0.35 mmol) is dissolved in dry THF (5 ml). 1-Methyl-piperidine-4-yl-magnesium chloride (3 eq, from step 2.2.1) is added drop wise. After completion of the addition of the Grignard reagent, the solution is allowed to stir over night. Control of the reaction is done by TLC (1% methanol/$CH_2Cl_2$). After the reaction is complete, the reaction is quenched first with acetic acid (5 ml), then with water (5 ml). The solvents are evaporated and the resulting carbinol is dehydrated with acetic anhydride (reflux, 4 h).

The acetic anhydride is evaporated and the residue is dissolved in 1 N KOH-solution. The free amine is extracted with methylene chloride, dried over $Na_2SO_4$ and the solvent is evaporated.

The crude product is purified with flash chromatography and then transferred into its hydrochloride by heating it in aqueous HCl (50 eq HCl, 5 ml, 4 h, 50° C.). The solvent is evaporated and the product dissolved in a mixture of tert. butyl alcohol and water (2 ml, 4:1 v/v) and lyophilized.

| Purity: | >98%; |
|---|---|
| Yield: | 25 mg, 20% |

2.2.4 Synthesis of 4-(6-Ethoxy-1-ethyl-thioxanthen-9-ylidene)-1-methyl-piperidine 6-Ethoxy-1-ethyl-thioxanthene-9-one (50 mg, 0.18 mmol) is dissolved in dry THF (5 ml). 1-Methyl-piperidine-4-yl-magnesium chloride (3 eq, from step 2.2.1) is added drop wise. After the first drop, the solution changed its color from light yellow to dark brown. After completion of the addition of the Grignard reagent, the solution is allowed to stir over night. Control of the reaction is done by TCL (1% methanol/$CH_2Cl_2$). After the reaction is complete, the reaction is quenched first with acetic acid (5 ml), then with water (5 ml). The solvents are evaporated and the resulting carbinol is dehydrated with acetic anhydride (reflux, 4 h).

The acetic anhydride is evaporated and the residue is dissolved in 1 N KOH-solution. The free amine is extracted with methylene chloride, dried over $Na_2SO_4$ and the solvent is evaporated.

The crude product is purified with flash chromatography and then transferred into its hydrochloride by heating it in aqueous HCl (50 eq HCl, 5 ml, 4 h, 50° C.). The solvent is evaporated and the product dissolved in a mixture of tert. butyl alcohol and water (2 ml, 4:1 v/v) and lyophilized.

| Purity: | >97%; |
|---|---|
| Yield: | 10.8 mg, 16% |

2.2.5 Synthesis of 4-(4-Ethoxy-selenoxanthene-9-ylidene)-1-methyl-piperidine 4-Ethoxy-1-selenoxanthene-9-one (50 mg, 0.16 mmol) is dissolved in dry THF (5 ml). 1-Methyl-piperidine-4-yl-magnesium chloride (3 eq, from step 2.2.1) is added drop wise. After the first drop, the solution changed its color from light yellow to dark brown. After completion of the addition of the Grignard reagent, the solution is allowed to stir over night. Control of the reaction is done by TCL (1% methanol/$CH_2Cl_2$). After the reaction is complete, the reaction is quenched first with acetic acid (5 ml), then with water (5 ml). The solvents are evaporated and the resulting carbinol is dehydrated with acetic anhydride (reflux, 4 h).

The acetic anhydride is evaporated and the residue is dissolved in 1 N KOH-solution. The free amine is extracted with methylene chloride, dried over $Na_2SO_4$ and the solvent is evaporated.

The crude product is purified with flash chromatography and then transferred into its hydrochloride by heating it in aqueous HCl (50 eq HCl, 5 ml, 4 h, 50° C.). The solvent is evaporated and the product dissolved in a mixture of tert. butyl alcohol and water (2 ml, 4:1 v/v) and lyophilized.

| Purity: | >97%; |
|---|---|
| Yield: | 28 mg, 46% |

2.3 Synthesis of compound 3-Ethoxy-9-(1-methyl-piperidine-4-ylidene)-9,10-dihydro-acridine Only step 2.3.3 must be performed under protecting atmosphere (argon)

2.3.1 Synthesis of 2-(3-Ethoxy-phenylamino)-benzoic acid m-Phenetidine (5 ml, 38.7 mmol) is added to a solution of KOH (7.385 g, 131.6 mmol), water (77 ml) and 2-iodobenzoic acid (9.6 g, 38.7 mmol). Powdered copper (77 mg, 1.22 µmol) is added and the mixture is refluxed under stirring over night (16 h).

The solution is filtered hot and is acidified with concentrated hydrochloric acid to precipitate the desired product. The crude product is purified with flash chromatography.

| Purity: | 95%; |
|---|---|
| Yield: | 3.0 g, 30% |

2.3.2 Synthesis of 3-Ethoxy-10H-acridin-9-one

To 2-(3-Ethoxyphenylamino)-benzoic acid (1.5 g, 4.2 mmol) polyphosphoric acid (20 g) is added and the mixture is heated under stirring to 120° C. After 4 h the solution is poured on crunched ice. The resulting aqueous solution is extracted with methylene chloride. The organic layer is again washed with water (2×) and brine (1×), dried with $Na_2SO_4$ and evaporated to dryness.

The crude product is purified with flash chromatography.

| Purity: | >95%; |
|---|---|
| Yield: | 200 mg, 14% |

2.3.3 Synthesis of 3-Ethoxy-9-(1-methyl-piperidin-4-ylidene)-9,10-dihydro-acridine 3-Ethoxy-10H-acridin-9-one (50 mg, 0.21 mmol) is dissolved in dry THF (5 ml). 1-Methyl-piperidine-4-yl-magnesium chloride (3 eq, from step 2.2.1) is added drop wise. After completion of the addition of the Grignard reagent, the solution is allowed to stir over night. Control of the reaction is done by TCL (1% methanoU/$CH_2Cl_2$). After the reaction is complete, the reaction is quenched first with acetic acid (5 ml), then with water (5 ml). The solvents are evaporated and the resulting carbinol is dehydrated with acetic anhydride (reflux, 4 h).

The acetic anhydride is evaporated and the residue is dissolved in 1 N KOH-solution. The free amine is extracted with methylene chloride, dried over $Na_2SO_4$ and the solvent is evaporated.

The crude product is purified with flash chromatography and then transferred into its hydrochloride by heating it in aqueous HCl (50 eq HCl, 5 ml, 4 h, 50° C.). The solvent is evaporated and the product dissolved in a mixture of tert. butyl alcohol and water (2 ml, 4:1 v/v) and lyophilized.

| | |
|---|---|
| Purity: | 99%; |
| Yield; | 22 mg, 32% |

EXAMPLE 3

Cloned Human 5-$HT_{2B}$ Receptor Binding Assay

The following describes an in vitro binding assay utilizing cloned 5-$HT_{2B}$ receptors radiolabeled with [$^3$H]-5HT.

Receptor Binding Assay

HEK 293 cells transiently transfected with an expression plasmid pXMD1-hu2B encoding the human 5-$HT_{2B}$ receptor (Schmuck et al. 1994 FEBS Lett 342:85-90) were used as described previously (Schmuck et al. 1996 Eur J Pharmacol 8:959-967). Two days after transfection cells were harvested, pelleted at 500 g for 5 min at 4° C., gently resuspended in ice-cold buffer 1 (50 mM TRIS pH 7.7, 4 mM $CaCl_2$) and homogenized using a Polytron PT 1200 tissue homogenizer (position 6 for 30 s). Cells were pelleted at 50,000 g, 4° C. for 10 min, washed with buffer 1 and pelleted again. The final pellet was resuspended in incubation buffer (50 mM TRIS pH 7.7, 4 mM $CaCl_2$, 10 μM pargyline and 0.1% by weight ascorbic acid). The binding assay consisted of 300 μl of membrane suspension (protein concentration=0.3 to 0.5 mg/ml), 150 μl of competing drug and 50 μl of [$^3$H]5-HT at a final concentration of 4 to 5 nM. The mixture was incubated at 37° C. for 30 min and the assay terminated by rapid filtration and two washing steps with 5 ml of cold 20 mM Tris-HCl pH 7.5, and 154 mM NaCl over Whatman GFB filters. Filters were counted by liquid scintillation. Non-specific binding was determined in the presence of an excess of 5-HT (100 μM). Bound radioligand represented less than 1% of free radioligand. In competition experiments, specific binding represented about 60% of total binding. Results expressed as $pK_i$ values are shown in Table 1.

Proceeding as in the example above the compounds of the present invention were found to have selective affinity for the 5-$HT_{2B}$ receptor.

EXAMPLE 4

5-$HT_{2A}$, 5-$HT_{2B}$, 5-$HT_{2C}$ Receptor Binding Methods

The following describes receptor binding methods in which ligands with high affinity for 5-$HT_{2B}$ receptors were counter screened at 5-$HT_{2A}$ and 5-$HT_{2C}$ receptors to demonstrate selectivity.

5-$HT_{2A}$ receptors were labelled with [$^3$H]ketanserin in human cortex, in HEK293 cells expressing a cloned human 5-$HT_{2A}$ receptor and in HEK293 cells expressing the rat 5-$HT_{2A}$ receptor. For competition binding studies the ligand concentration was approximately 0.1 nM. For saturation binding studies concentrations of radioligand ranged from 0.01 nM to 2.0 nM. Assays were conducted in 0.5 ml of assay buffer (50 mM Tris-HCl, 4 mM calcium chloride, 0.1% by weight ascorbic acid) (pH 7.4 at 4° C.). Non-specific binding was defined with 10 mM unlabelled ketanserin. After a 60 min incubation at 32° C., membranes were harvested onto filters treated with 0.1% by weight of polyethylenimine and the bound radioactivity was determined.

Human 5-$HT_{2B}$ receptors were labelled in HEK293 cells as described above except that the radioligand was [$^3$H]-5HT and that the assay buffer contained pargyline in a concentration of 10 mM and 0.1% by weight of ascorbic acid. For competition binding studies the radioligand concentration was approximately 0.4 nM while for saturation binding studies the concentration of [$^3$H]-5HT ranged from 0.05 to 8 nM. Non-specific binding was defined with 10 mM 5-HT. Incubations were for 120 min at 4° C.

5-$HT_{2C}$ receptors were labelled in choroid plexus, Cos-7 cells expressing the human 5-$HT_{2C}$ receptor and in NIH-3T3 expressing the rat 5-$HT_{2A}$ receptor.

Assays were conducted as described for the 5-$HT_{2A}$ receptor except that the radioligand was [$^3$H]mesulergine. The radioligand concentration for competition studies was approximately 0.2 nM while for saturation binding studies the concentration ranged from 0.1 to 18 DM. Non-specific binding was defined with 10 μM unlabelled mesulergine.

Competition radioligand binding data was analyzed using a four-parameter logistic equation and iterative curve-fitting techniques to obtain estimates of the $IC_{50}$ and Hill slope. Kd values, determined from saturation binding studies were then used to calculate inhibition dissociation constants (Ki).

Proceeding as in the example above the compounds of the present invention were found to have selective affinity for the 5-$HT_{2B}$ receptor. Results are shown in Table 1

EXAMPLE 5

5-$HT_{2B}$ Receptor Tissue Based Functional Assay

The following describes an in vitro functional assay characterizing 5-HT receptors (the putative 5-$HT_{2B}$) in rat stomach fundus longitudinal muscle (Baxter et al. 1994 Brit J Pharmacol 112:323-331).

Strips of longitudinal muscle were obtained from the stomach fundus of male Sprague Dawley rats. The mucosa was removed and the strips were suspended with a resting tension of 1 g in oxygenated (95% $O_2$/5% $CO_2$) Tyrode solution at 37° C. The composition of the Tyrode solution was as follows (mM): NaCl 136.9; KCl 2.7; $NaH_2PO_4$ 0.4; $MgCl_2$ 1.0; glucose 5.6; $NaHCO_3$ 11.9; $CaCl_2$ 1.8.

Concentration-response curves to 5-HT receptor agonists were constructed under conditions where cyclooxygenase activities were inactivated by 3 μm indomethacin, monoamine oxidase activities inactivated by 0.1 mM pargyline, and uptake mechanisms inactivated by 30 μM cocaine and 30 μM corticosterone.

Effects of drugs were monitored by tension transducers and recorded on polygraph recorders. Tissue response was measured as changes in isometric tension (g). The mean potency ($EC_{50}$) and maximum response were evaluated by standard iterative curve fitting procedures.

Effects of antagonists were determined by measuring dextral shifts to the agonist concentration-response curve after equilibration of the antagonists for at least 1 h. Concentration ratios were measured at half maximal response levels and single concentration antagonist affinities were determined by the equation:

$$KB = \frac{\text{antagonist concentration}}{\text{concentration ratio}}$$

Schild regression analysis was employed with multiple antagonist concentrations when the compound showed competitive behavior.

Proceeding as in the example above, the compounds of the present invention were found to be selective antagonists at the 5-$HT_{2B}$ receptor.

EXAMPLE 6

Cloned Human $H_1$, $H_2$, and $H_3$ Receptor Binding Assay

COS-7 cells were transiently transfected with an expression plasmid pCineohH1, pCineohH2, pCineohH3 and pCineohH4 encoding the human Histamine H1, H2, H3 or H4 receptor, respectively. Transfected cells were harvested after 48 h, homogenized in ice-cold 50 mM $Na_2$/potassium phosphate buffer (pH 7.4) and used for radioligand binding studies. Cell homogenates (40-50 µg of protein) were incubated for 30 min at 25° C. in 50 mM $Na_2$/potassium phosphate buffer (pH 7.4) in 400 µl with the various concentrations of either [$^3$H]-mepyramine, [$^3$H]-thiotidine, [$^3$H]-R-α-Methylhistamine, and [$^3$H]-pyramilamine for cells expressing recombinant human H1, H2, H3 and H4 receptors, respectively. The nonspecific binding was defined in the presence of 1 µM mianserin. In displacement studies, cell homogenated were incubated either with 1 nM [$^3$H]-mepyramine, 15 nM [$^3$H]-thiotidine, 0.5 nM [$^3$H]-R-α-Methylhistamine, or 15 nM [$^3$H]-pyramilamine and increasing concentrations of competing ligands. The incubations were stopped by rapid dilution with 3 ml of ice-cold 50 mM $Na_2$/potassium phosphate buffer (pH 7.4). The bound radioactivity was separated by filtration through Whatman GF/C filters that had been treated with 0.3% polyethyleneimine. Filters were washed twice in 3 ml of buffer and radioactivity retained on the filters was measured by liquid scintillation counting.

The concentration of 1-methyl-4-(3-ethoxy-9H-thioxanthene-9-ylidene)-piperidine producing 50% inhibition of binding ($IC_{50}$) was determined using iterative curve fitting techniques.

Proceeding as in the example above each of the compounds of the present invention were found to have low affinity for the human $H_1$ receptor.

EXAMPLE 7

Human Histamine $H_1$ Receptor Functional Assay

For the measurement of the [$^3$H]-inositol phosphate formation transiently transfected HEK-293 cells were seeded in 24 well plates and labeled to equilibrium with myo-[2-$^3$H]-inositol (3 µCi/ml) for an additional 24 hours in growth medium. The medium was aspirated and cells were washed once with 500 µl HBS-buffer (130 mM NaCl, 900 µM $NaH_2PO_4$, 800 µM $MgSO_4$, 5.4 mM KCl, 1.8 mM $CaCl_2$, 25 mM Glucose in 20 mM HEPES pH 7.4). Two min after applying 20 mM Li$^+$ the cells were stimulated by addition of agonist in HBS-buffer. The incubation was stopped by aspiration off the culture medium and the addition of cold 10 mM formic acid. [$^3$H]inositol phosphates were isolated by anion exchange chromatography (Seuwen et al. 1988 *EMBO J*

7:161-168). The pKB value was calculated according to the formula: $pK_B = \log(A'/A - 1) - \log[B]$, where $A'/A$ is the ratio of the agonist concentrations ($EC_{50}$ in the presence/$EC_{50}$ in the absence of antagonist) and [B] the concentration of antagonist.

Proceeding as in the example above the compounds of the present invention were found to be antagonists of lower potency at the human $H_1$ receptor. Results are shown in Table 1.

TABLE 1

| Receptor Affinity: pK Values of the compounds | | | | |
|---|---|---|---|---|
| Compound | 5-$HT_{2A}$ receptor | 5$HT_{2B}$ receptor | $H_1$ receptor | 5$HT_{2C}$ receptor |
| 4-(6-Ethoxy-1-methoxy-thioxanthen-9-yliden)-1-methyl-piperidine | 8.99 | 10.35 | 8.43 | 7.77 |
| 4-(6-Ethoxy-1-hydroxy-thioxanthen-9-yliden)-1-methyl-piperidine | 8.82 | 10.94 | 7.44 | 7.86 |
| 4-(6-Isopropyl-1-methoxy-thioxanthen-9-yliden)-1-methyl-piperidine | 9.13 | 9.77 | 7.98 | 7.79 |
| 4-(6-Isopropyl-1-hydroxy-thioxanthen-9-yliden)-1-methyl-piperidine | 9.11 | 9.92 | 7.45 | 7.52 |
| 3-Ethoxy-9-(1-methyl-piperidine-4-ylidene)-9,10-dihydro-acridine | 8.93 | 9.13 | 7.53 | 7.43 |
| 4-(6-Methoxy-1-methoxy-thioxanthen-9-yliden)-1-methyl-piperidine | 10.37 | 11.06 | 9.89 | 8.81 |

The results of Table 1 show, that the compounds of the present invention have a selective affinity for the 5$HT_{2B}$ receptor, particularly have a much higher affinity for the 5$HT_{2B}$ receptor than for the H1 and the 5$HT_{2C}$ receptor.

What is claimed is:

1. A compound according to the formula

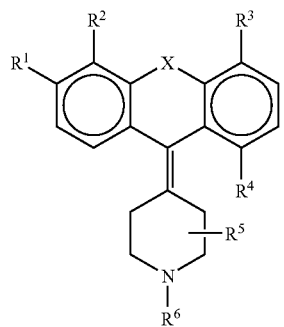

or a pharmaceutically acceptable salt thereof, wherein $R^1$ is selected from the group consisting of ethyl, propyl, isopropyl, butyl, isobutyl, pentyl, hexyl, ethoxy, propoxy, isopropoxy, butoxy, isobutoxy, phenoxy, trifluoromethyl, trifluoromethoxy, amino, dimethylamino, —CON(CH$_3$)$_2$ and —CON(C$_2$H$_5$)$_2$;

$R^2$ is a methyl, ethyl, propyl, isopropyl, butyl, isobutyl, pentyl, hexyl, hydroxy or hydrogen, or $R^1$ and $R^2$ together form a five-membered heterocycle, wherein a heteroatom in said heterocycle is an oxygen atom;

R³ is selected from the group consisting of methyl, ethyl, propyl, isopropyl, butyl isobutyl, pentyl, hexyl, hydroxy and hydrogen;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

R⁵ is methyl or hydrogen;

R⁶ is methyl or ethyl; and

X is N or Se;

wherein said compound is a selective 5-HT2B receptor antagonist relative to 5-HT2A and 5-HT2C receptors.

2. The compound of claim 1, wherein

R¹ is an isopropyl, dimethylamino, or ethoxy,

R² is ethyl or hydrogen, or R¹ and R² together form a five-membered heterocycle, wherein a lieteroatom in said heterocycle is an oxygen atom, R³ is ethyl or hydrogen, R⁴ is methoxy, hydroxy, ethyl, methyl or hydrogen, R⁵ is methyl or hydrogen, R⁶ is methyl, and X is N or Se, or a pharmaceutically acceptable salt thereof.

3. The compound of claim 1, wherein R¹ is an isopropyl, dimethylamino, or ethoxy group.

4. A compound selected from the group consisting of 4-(6-Isopropyl- 1-methoxy-thioxanthen-9-yliden)-1 -methyl-piperidine, 4-(6-Ethoxy-1-ethyl-thioxanthen-9-yliden) -1-methyl-piperidine, 4-(6-Ethoxy- 1 -methoxy-thioxanthen-9-yliden)-1-methyl-piperidine, 4-(6-Methoxy-1-methoxy-thioxanthen-9-yliden)-1 -methyl-piperidine, 4-(6-Dimethylamino- 1-merhoxy-thioxanthen-9-yliden)-1-methyl-piperidine, 4-(6-Dimethylamino-1-hydroxy -thioxanthen-9-yliden)-1 -methyl-piperidine, 4-(3-Ethoxy-selenoxanthen-9-yliden)-1-methyl -piperidine, 4-(3-Ethoxy-1-methoxy-selenoxanthen-9-yliden)-1-methyl-piperidine, 4-(3-Ethoxy-1-hydroxy-selenoxanthen-9-yliden)-1-methyl-piperidine, 3-Ethoxy-9-(1-methyl-piperidine-4-ylidene)-9,10-dihydro-acridine, 6-Ethoxy-1-methoxy-9-(1-methyl-piperidine-4-ylidene)-9,10-dihydro-acridine, 6-Ethoxy-1-hydroxy-9-(1 -methyl-piperidine-4-ylidene)-9, 10-dihydro-acridine, 4-(3-Ethoxy-5-ethyl-thioxanthen-9-yliden)-1-methyl-piperidine, 4-(3-Ethoxy-4-methyl -thioxanthen-9-yliden)-1-methyl-piperidine, 4-(3 -Ethoxy-4-ethyl-thioxanthen-9-yliden)-1-methyl -piperidine, 4-(3-Ethoxy-thioxanthen-9-yliden)- 1,3-dimethyl-piperidine, 4-(3,4-(Cyclopent-3'-oxy-1'-eno)-thioxanthen-9-yliden)-1-methyl-piperidine, 4-(3,4-(Cyclopent-4 '-oxy-1'-eno) -thioxanthen-9-yliden)-1-methyl-piperidine and 4-(3,4-(Cyclopent-5 '-oxy-1 '-eno)-thioxanthen-9-ylidcn)-1-methyl-piperidine, wherein said compound is a selective 5-HT2B receptor antagonist.

5. A pharmaceutical composition, comprising one or more pharmaceutically acceptable carriers; and a compound according to the formula:

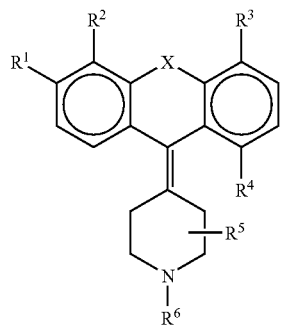

or a pharmaceutically acceptable salt thereof, wherein

R¹ is selected from the group consisting of methyl, ethyl, propyl, isopropyl, butyl, isobutyl, pentyl, hexyl, methoxy, ethoxy, propoxy, isopropoxy, butoxy, isobutoxy, phenoxy, trifluoromethyl, trifluoromethoxy, amino, dimethylamino, bromine, —CON(CH₃)₂ and —CON(C₂H₅)₂;

R² is a methyl, ethyl, propyl, isopropyl, butyl, isobutyl, pentyl, hexyl, hydroxy or hydrogen, or R¹ and R² are forming a five-membered heterocycle, wherein a heteroatom in said heterocycle is an oxygen atom;

R³ is selected from the group consisting of methyl, ethyl, propyl, isopropyl, butyl isobutyl, pentyl, hexyl, hydroxy and hydrogen;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl propyl, isopropyl, butyl and hydrogen;

R⁵ is methyl or hydrogen;

R⁶ is methyl or ethyl;

and X is N or Se, or a phannaceutically acceptable salt thereof;

wherein said compound is a selective 5-HT2B receptor antagonist.

6. The phamaceutical composition of claim 5, wherein

R¹ is selected from the group consisting of ethyl, propyl, isopropyl, butyl, isobutyl, pentyl, hexyl, ethoxy, propoxy, isopropoxy, butoxy, isobutoxy, phenoxy, trifluoromethyl, trifluoromethoxy, amino, dimethylamino, —CON(CH₃)₂ and —CON(C₂H₅)₂;

R² is a methyl, ethyl, propyl, isopropyl, butyl, isobutyl, pentyl, hexyl, hydroxy or hydrogen, or R¹ and R² together form a five-membered heterocycle, wherein a heteroatom in said heterocycle is an oxygen atom;

R³ is selected from the group consisting of methyl, ethyl, propyl, isopropyl, butyl isobutyl, pentyl, hexyl, hydroxy and hydrogen;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

R⁵ is methyl or hydrogen;

R⁶ is methyl or ethyl; and

X is N or Se;

wherein said compound is a selective 5-HT2B receptor antagonist relative to 5-HT2A and 5-HT2C receptors.

7. The pharmaceutical composition of claim 6, wherein
R¹ is an isopropyl, dimethylamino, or ethoxy group,
R² is ethyl or hydrogen, or R¹ and R² together form a five-membered heterocycle, wherein a heteroatom in said heterocycle is an oxygen atom,
R³ is ethyl or hydrogen,
R⁴ is methoxy, hydroxy, ethyl, methyl or hydrogen,
R⁵ is methyl or hydrogen,
R⁶ is methyl, and
X is N or Se, or a pharmaceutically acceptable salt thereof.

8. The composition of claim 5, wherein R³ is ethyl or hydrogen.

9. The composition of claim 5, wherein R⁴ is methoxy, hydroxy, ethyl, methyl or hydrogen.

10. The composition of claim 5, wherein R⁵ is methyl or hydrogen.

11. The composition of claim 5, wherein R¹ is selected from the group consisting of methoxy, methyl, bromo, isopropyb and trifluoromethyl.

12. A method of preparation of a compound according to claim 1, comprising reacting a compound of the following formula:

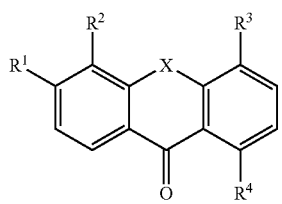

with an alkyl magnesium halide Grignard reagent, wherein R¹, R², R³, R⁴ and X are as defined in claim 1.

13. A method for selectively binding a 5-HT2B receptor comprising administering to the mammal a pharmaceutically effective amount of a composition according to claim 5.

14. A compound according to the formula

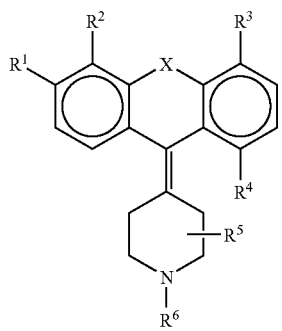

or a pharmaceutically acceptable salt thereof, wherein

R¹ is selected from the group consisting of ethyl, propyl, isopropyl, butyl, isobutyl, pentyl, hexyl, ethoxy, propoxy, isopropoxy, butoxy, isobutoxy, phenoxy, trifluoromethyl, trifluoromethoxy, amino, dimethylamino, —CON(CH₃)₂ and —CON(C₂H₅)₂;

R² is a methyl, ethyl, propyl, isopropyl, butyl, isobutyl, pentyl, hexyt, or hydroxy, or R¹ and R² together form a five-membered heterocycle, wherein a heteroatom in said heterocycle is an oxygen atom;

R³ is selected from the group consisting of methyl, ethyl, propyl, isopropyl, hutyl isobutyl, pentyl, hexyl, hydroxy and hydrogen;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

R⁵ is methyl or hydrogen;

R⁶ is methyl or ethyl; and

X is S;

wherein said compound is a selective 5-HT2B receptor antagonist relative to 5-HT2A and 5-HT2C receptors.

15. A compound according to the formula

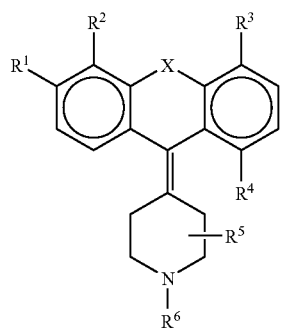

or a pharmaceutically acceptable salt thereof, wherein

R¹ is selected from the group consisting of ethyl, propyl, isopropyl, butyl, isobutyl, pentyl, hexyl, ethoxy, propoxy, isopropoxy, butoxy, isobutoxy, phenoxy, trifluoromethyl, trifluoromethoxy, amino, dimethylamino, —CON(CH₃)₂ and —CON(C₂H₅)₂;

R² is a methyl, ethyl, propyl, isopropyl, butyl, isobutyl, pentyl, hexyl, hydroxy or hydrogen, or R¹ and R² together form a five-membered heterocycle, wherein a heteroatom in said heterocycle is an oxygen atom;

R³ is selected from the group consisting of methyl, ethyl, propyl, isopropyl, butyl isobutyl, pentyl, hexyl, and hydroxy;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

R⁵ is methyl or hydrogen;

R⁶ is methyl or ethyl; and

X is S;

wherein said compound is a selective 5-HT2B receptor antagonist relative to 5-HT2A and 5-HT2C receptors.

16. A compound according to the formula

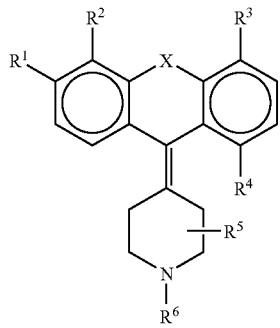

or a pharmaceutically acceptable salt thereof, wherein $R^1$ is selected from the group consisting of ethyl, propyl, isopropyl, butyl, isobutyl, pentyll, hexyl, ethoxy, propoxy, isopropoxy, butoxy, isobutoxy, phenoxy, trifluoromethyl, trifluoromethoxy, amino, dimethylamino, —CON(CH$_3$)$_2$ and —CON(C$_2$H$_5$)$_2$;

$R^2$ is a methyl, ethyl, propyl, isopropyl, butyl, isobutyl, pentyt, hexyl, hydroxy or hydrogen, or $R^1$ and $R^2$ together form a five-membered heterocycle, wherein a heteroatom in said heterocycle is an oxygen atom;

$R^3$ is selected from the group consisting of methyl, ethyl, propyl, isopropyl, butyl isobutyl, pentyl, hexyl, hydroxy and hydrogen;

$R^4$ is selected from the group consisting of hydroxy, methoxy, ethoxy, propoxy, isopropoxy, butoxy, isobutoxy, trifluoromethyl, amino, dimethytamino, diethylamino, fluorine, bromine, methyl, ethyl, propyl, isopropyl, and butyl;

$R^5$ is methyl or hydrogen;

$R^6$ is methyl or ethyl; and

X is S;

wherein said compound is a selective 5-HT2B receptor antagonist relative to 5-HT2A and 5-HT2C receptors.

17. A compound according to the formula

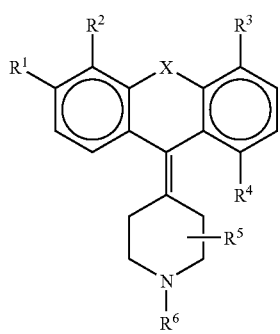

or a pharmaceutically acceptable salt thereof, wherein $R^1$ is selected from the group consisting of ethyl, propyl, isopropyl, butyl, isobutyl, pentyl, hexyl, ethoxy, propoxy, isopropoxy, butoxy, isobutoxy, phenoxy, trifluoromethyl, trifluoromethoxy, amino, dimethylanino, —CON(CH$_3$)$_2$ and —CON(C$_2$H$_5$)$_2$;

$R^2$ is a methyl, ethyl, propyl, isopropyl, butyl, isobutyl, pentyl, hexyl, hydroxy or hydrogen, or $R^1$ and $R^2$ together form a five-membered heterocycle, wherein a heteroatom in said heterocycle is an oxygen atom;

$R^3$ is selected from the group consisting of methyl, ethyl, propyl, isopropyl, butyl isobutyl, pentyl, hexyl, hydroxy and hydrogen;

$R^4$ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

$R^5$ is methyl;

$R^6$ is methyl or ethyl; and

X is S;

wherein said compound is a selective 5-HT2B receptor antagonist relative to 5-HT2A and 5-HT2C receptors.

18. A pharmaceutical composition, comprising one or more pharmaceutically acceptable carriers; and a compound according to the formula:

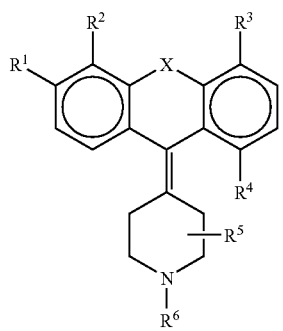

or a pharmaceutically acceptable salt thereof, wherein $R^1$ is selected from the group consisting of methyl, ethyl, propyl, isopropyl, butyl, isobutyl, pentyl, hexyl, methoxy, ethoxy, propoxy, isopropoxy, butoxy, isobutoxy, phenoxy, trifluoromethyl, trifluoromethoxy, amino, dimethylamino, bromine, —CON(CH$_3$)$_2$ and —CON(C$_2$H$_5$)$_2$;

$R^2$ is a methyl, ethyl, propyl, isopropyl, butyl, isobutyl, pentyl, hexyl, or hydroxy, or $R^1$ and $R^2$ together form a five-membered heterocycle, wherein a heteroatom in said heterocycle is an oxygen atom;

$R^3$ is selected from the group consisting of methyl, ethyl, propyl, isopropyl, butyl isobutyl, pentyl, hexyl, hydroxy and hydrogen;

$R^4$ is selected from the group consisting of hydroxy, methoxy, ethoxy, propoxy, isopropoxy, butoxy, isobtitoxy, trifluoromethyl, amino, dimethylamino, diethylamino, fluorine, bromine, methyl, ethyl, propyl, isopropyl, butyl and hydrogen;

$R^5$ is methyl or hydrogen;

$R^6$ is methyl or ethyl; and

X is S;

wherein said compound is a selective 5-HT2B receptor antagonist relative to 5-HT2A and 5-HT2C receptors.

19. A pharmaceutical composition, comprising one or more pharmaceutically acceptable carriers; and a compound according to the formula:

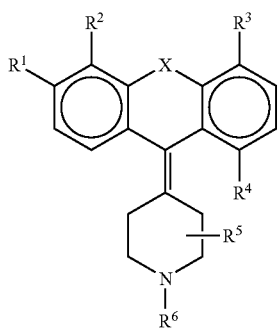

or a pharmaceutically acceptable salt thereot wherein

R¹ is selected from the group consisting of methyl, ethyl, propyl, isopropyl, butyl, isobutyl, pentyl, hexyl, methoxy, ethoxy, propoxy, isopropoxy, butoxy, isobutoxy, phenoxy, trifluoromethyl, trifluoromethoxy, amino, dimethylamino, bromine, —CON(CH₃)₂ and —CON(C₂H₅)₂;

R² is a methyl, ethyl, propyl, isopropyl, butyl, isobutyl, pentyl, hexyl, hydroxy or hydrogen, or R¹ and R² together form a five-membered heterocycle, wherein a heteroatom in said heterocycle is an oxygen atom;

R³ is selected from the group consisting of methyl, ethyl, propyl, isopropyl, butyl isobutyl, pentyl, hexyl, and hydroxy; R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

R⁵ is methyl or hydrogen;
R⁶ is methyl or ethyl; and
X is S;

wherein said compound is a selective 5-HT2B receptor antagonist relative to 5-HT2A and 5-HT2C receptors.

20. A pharmaceutical composition, comprising one or more pharmaceutically acceptable carriers; and a compound according to the formula:

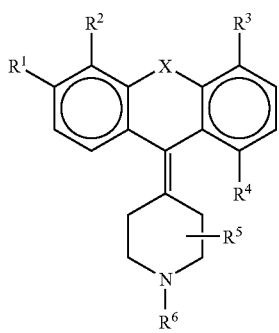

or a pharmaceutically acceptable salt thereof, wherein

R¹ is selected from the group consisting of methyl, ethyl, propyl, isopropyl, butyl, isobutyl, pentyl, hexyl, methoxy, ethoxy, propoxy, isopropoxy, butoxy, isobutoxy, phenoxy, trifluoromethyl, trifluoromethoxy, amino, dimethylamino, bromine, —CON(CH₃)₂ and —CON(C₂H₅)₂;

R² is a methyl, ethyl, propyl, isopropyl, butyl, isobutyl, pentyl, hexyl, hydroxy or hydrogen, or R¹ and R² together form a five-membered heterocycle, wherein a heteroatom in said heterocycle is an oxygen atom;

R³ is selected from the group consisting of methyl, ethyl, propyl, isopropyl, butyl isobutyl, pentyl, hexyl, hydroxy and hydrogen;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, and butyl;

R⁵ is methyl or hydrogen;
R⁶ is methyl or ethyl; and
X is S;

wherein said compound is a selective 5-HT2B receptor antagonist relative to 5-HT2A and 5-HT2C receptors.

21. A pharmaceutical composition, comprising one or more pharmaceutically acceptable carriers; and a compound according to the formula:

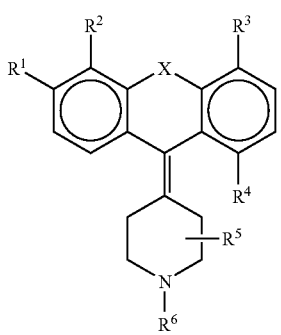

or a pharmaceutically acceptable salt thereot wherein

R¹ is selected from the group consisting of methyl, ethyl, propyl, isopropyl, butyl, isobutyl, pentyl, hexyl, methoxy, ethoxy, propoxy, isopropoxy, butoxy, isobutoxy, phenoxy, trifluoromethyl, trifluoromethoxy, amino, dimethylamino, bromine, —CON(CH₃)₂ and —CON(C₂H₅)₂;

R² is a methyl, ethyl, propyl, isopropyl, butyl, isobutyl, pentyl, hexyl, hydroxy or hydrogen, or R¹ and R² together form a five-membered heterocycle, wherein a heteroatom in said heterocycle is an oxygen atom;

R³ is selected from the group consisting of methyl, ethyl, propyl, isopropyl, butyl isobutyl, pentyl, hexyl, hydroxy and hydrogen;

R⁴ is selected from the group consisting of hydroxy, methoxy, ethoxy, propoxy, isopropoxy, butoxy, isobutoxy, trifluoromethyl, amino, dimethylamino, diethylamino, fluorine, bromine, methyl, ethyl, propyl, isopropyl, butyl and hydrogen;

R⁵ is methyl;
R⁶ is methyl or ethyl; and
X is S;

wherein said compound is a selective 5-HT2B receptor antagonist relative to 5-HT2A and 5-HT2C receptors.

* * * * *

UNITED STATES PATENT AND TRADEMARK OFFICE
CERTIFICATE OF CORRECTION

PATENT NO. : 7,511,064 B2
APPLICATION NO. : 11/379353
DATED : March 31, 2009
INVENTOR(S) : Lubbert et al.

It is certified that error appears in the above-identified patent and that said Letters Patent is hereby corrected as shown below:

On Column 1, Line 7, please change "application" to --Application--.

On Column 1, Line 17, please change "5-HT$_2$B" to --5-HT$_{2B}$--.

On Column 1, Line 47, please change "human-brain," to --human brain,--.

On Column 2, Line 53, please change "R1 and R2" to --R$^1$ and R$^2$--.

On Column 2, Line 54, please change "butyl" to --butyl,--.

On Column 4, Line 4-5 (Approx.), please change

"4-(6-Ethoxy-l-methoxy-thiox-9-yliden)-1-methyl-piperidine," to

--4-(6-Ethoxy-1-methoxy-thioxanthen-9-yliden)-1-methyl-piperidine,--.

On Column 4, Line 54, please change "Hi" to --H1--.

On Column 7, Line 32, please change "HI" to --H1--.

On Column 8, Line 25, please change "][BS" to --IBS--.

On Column 9, Line 62, please change "5-HT2$_c$" to --5-HT$_{2C}$--.

On Column 12, Line 30-65, please change

" "

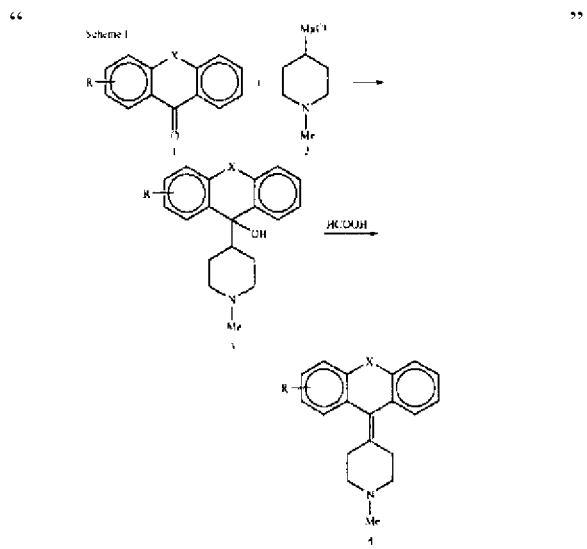

UNITED STATES PATENT AND TRADEMARK OFFICE
CERTIFICATE OF CORRECTION

PATENT NO. : 7,511,064 B2
APPLICATION NO. : 11/379353
DATED : March 31, 2009
INVENTOR(S) : Lubbert et al.

It is certified that error appears in the above-identified patent and that said Letters Patent is hereby corrected as shown below:

to

-- 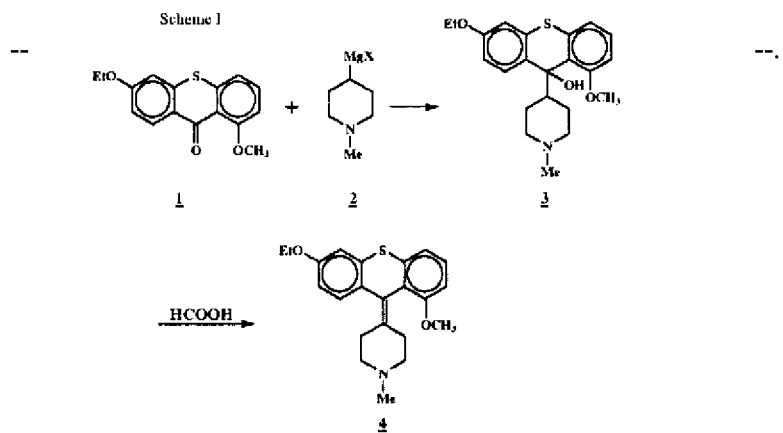 --.

On Column 13, Line 6 (Approx.), please change "isomeres" to --isomers--.

On Column 15, Line 16, please change "Dienthyl" to --Diethyl--.

On Column 17, Line 14, please change "CH2Cl2" to --$CH_2Cl_2$--.

On Column 18, Line 2, please change "yliden -1" to --yliden)-1--.

On Column 20, Line 59, please change "(1% methanoU/$CH_2Cl_2$)." to --(1% methanol/$CH_2Cl_2$).--.

On Column 22, Line 31, after "Table 1" insert --.--.

On Column 24, Line 1, please change "pKB" to --$pK_B$--.

On Column 24, Line 36 (Approx.), please change "H1" to --$H_1$--.

On Column 25, Line 2, in Claim 1, please change "butyl isobutyl" to --butyl, isobutyl--.

On Column 25, Line 21, in Claim 2, please change "lieteroatom" to --heteroatom--.

UNITED STATES PATENT AND TRADEMARK OFFICE
CERTIFICATE OF CORRECTION

PATENT NO.       : 7,511,064 B2
APPLICATION NO.  : 11/379353
DATED            : March 31, 2009
INVENTOR(S)      : Lubbert et al.

It is certified that error appears in the above-identified patent and that said Letters Patent is hereby corrected as shown below:

On Column 25, Line 40 (Approx.), in Claim 4, please change "merhoxy" to --methoxy--.

On Column 25, Line 60-61, in Claim 4, please change "4-(3,4-(Cyclopent-5 '-oxy-1 '-eno)-thioxanthen-9-ylidcn)-l-methyl-piperidine" to --4-(3,4-(Cyclopent-5'-oxy-1'-eno)-thioxanthen-9-yliden)-1-methyl-piperidine--.

On Column 26, Line 29, in Claim 5, please change "butyl isobutyl" to --butyl, isobutyl--.

On Column 26, Line 34 (Approx.), in Claim 5, please change "ethyl propyl" to --ethyl, propyl--.

On Column 26, Line 39, in Claim 5, please change "phannaceutically" to --pharmaceutically--.

On Column 26, Line 44, in Claim 6, please change "phamaceutical" to --pharmaceutical--.

On Column 26, Line 55, in Claim 6, please change "butyl isobutyl" to --butyl, isobutyl--.

On Column 27, Line 22-23, in Claim 11, please change "isopropyb" to --isopropyl--.

On Column 28, Line 2, in Claim 14, please change "hexyt" to --hexyl--.

On Column 28, Line 7, in Claim 14, please change "hutyl isobutyl" to --butyl, isobutyl--.

On Column 28, Line 54, in Claim 15, please change "butyl isobutyl" to --butyl, isobutyl--.

UNITED STATES PATENT AND TRADEMARK OFFICE
CERTIFICATE OF CORRECTION

PATENT NO. : 7,511,064 B2
APPLICATION NO. : 11/379353
DATED : March 31, 2009
INVENTOR(S) : Lubbert et al.

It is certified that error appears in the above-identified patent and that said Letters Patent is hereby corrected as shown below:

On Column 29, Line 22, in Claim 16, please change "pentyll" to --pentyl--.

On Column 29, Line 28, in Claim 16, please change "pentyt" to --pentyl--.

On Column 29, Line 33, in Claim 16, please change "butyl isobutyl" to --butyl, isobutyl--.

On Column 29, Line 37, in Claim 16, please change "dimethytamino" to --dimethylamino--.

On Column 30, Line 1, in Claim 17, please change "dimethylanino" to --dimethylamino--.

On Column 30, Line 8, in Claim 17, please change "butyl isobutyl" to --butyl, isobutyl--.

On Column 30, Line 53, in Claim 18, please change "butyl isobutyl" to --butyl, isobutyl--.

On Column 30, Line 56, in Claim 18, please change "isobtitoxy" to --isobutoxy--.

On Column 31, Line 16, in Claim 19, please change "thereot" to --thereof,--.

On Column 31, Line 29 (Approx.), in Claim 19, please change "butyl isobutyl" to --butyl, isobutyl--.

On Column 32, Line 6, in Claim 20, please change "butyl isobutyl" to --butyl, isobutyl--.

UNITED STATES PATENT AND TRADEMARK OFFICE
CERTIFICATE OF CORRECTION

PATENT NO. : 7,511,064 B2
APPLICATION NO. : 11/379353
DATED : March 31, 2009
INVENTOR(S) : Lubbert et al.

It is certified that error appears in the above-identified patent and that said Letters Patent is hereby corrected as shown below:

On Column 32, Line 38, in Claim 21, please change "thereot" to --thereof,--.

On Column 32, Line 50, in Claim 21, please change "butyl isobutyl" to --butyl, isobutyl--.

Signed and Sealed this

Twenty-fourth Day of November, 2009

David J. Kappos
*Director of the United States Patent and Trademark Office*